United States Patent [19]
de la Chapelle et al.

[11] Patent Number: 5,837,443
[45] Date of Patent: Nov. 17, 1998

[54] DIAGNOSTIC METHOD EMPLOYING MSH2 PROTEIN

[75] Inventors: Albert de la Chapelle, Bergmansgatan, Finland; Bert Vogelstein; Kenneth W. Kinzler, both of Baltimore, Md.

[73] Assignee: The Johns Hopkins University, Baltimore, Md.

[21] Appl. No.: 457,374

[22] Filed: Jun. 1, 1995

Related U.S. Application Data

[60] Division of Ser. No. 160,295, Dec. 2, 1993, which is a continuation-in-part of Ser. No. 56,546, May 5, 1993, Pat. No. 5,492,808.

[51] Int. Cl.$^6$ .............................. C12Q 1/25; C07K 14/47
[52] U.S. Cl. ................... 435/4; 435/40.5; 530/350
[58] Field of Search ..................... 435/4, 40.5; 530/350

[56] References Cited

U.S. PATENT DOCUMENTS 5,075,217  12/1991  Weber ........................................ 435/6

OTHER PUBLICATIONS

Richard Fishel, et al., The Human Mutator Gene Homolog MS H2 and Its Association with Hereditary Nonpolyposis Colon Cancer, Cell, vol. 75, 1027–1038, Dec. 3, 1993.

Scc–1, a novel colon cancer susceptibility gene in the mouse: linkage to CD44 (Ly–24, Pgp–1) on chromosone 2, Corina J. A. Moen, et al., Oncogene (1992), 7, 563–566, Macmilllan Press Ltd. 1992.

Strand et al., "Destabilization of Tracts of Simple Repetitive DNA in Yeast by Mutations Affecting DNA Mismatch Repair", *Nature,* 365:274–276 (1993).

Kunkel, "Slippery DNA and Diseases", *Nature,* 365:207–208 (1993).

Parsons, et al., "Hypermutability and Mismatch Repair Deficiency in RER+ Tumor Cells", *Cell,* 75:1227–1236 (1993).

Päivi Peltomäki, et al., Genetic Mapping of a Locus Predisposing to Human Colorectal Cancer, Science, vol. 260, 7 May 1993 pp. 810–812.

Lauri A. Aaltonen, et al., Clues to the Pathogenesis of Familial Colorectal Cancer, Science, vol. 260, 7 May 1993, pp. 812–816.

S.N. Thibodeau, et al., Microsatellite Instability in Cancer of the Proximal Colon, Science, vol. 260, 7 May 1993, 816–819.

Rick Weise, Gene for Colon Cancer Identified, Scientists Foresee Simple Blood Test for Hereditary Forms of Disease, Washington Post, Dec. 3, 1993.

*Primary Examiner*—Robert A. Wax
*Assistant Examiner*—Kawai Lau
*Attorney, Agent, or Firm*—Banner & Witcoff, Ltd.

[57] ABSTRACT

The human MSH2 gene, responsible for hereditary non-polyposis colorectal cancer, was identified by virtue of its homology to the MutS class of genes, which are involved in DNA mismatch repair. The sequence of cDNA clones of the human gene are provided, and the sequence of the gene can be used to demonstrate the existence of germ line mutations in hereditary non-polyposis colorectal cancer (HNPCC) kindreds, as well as in replication error[+] (RER[+]) tumor cells.

3 Claims, 10 Drawing Sheets

FIG. 2A   FIG. 2B   FIG. 2C   FIG. 2D
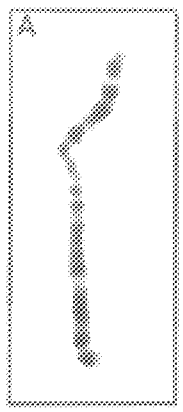 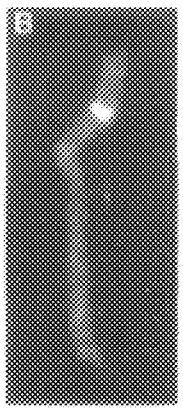 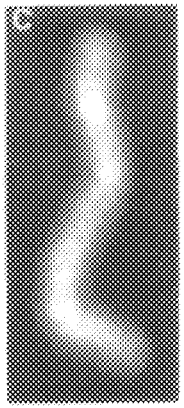 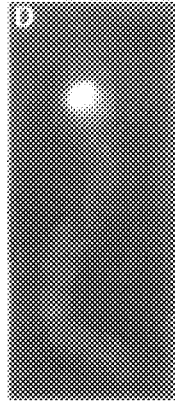
FIG. 2E
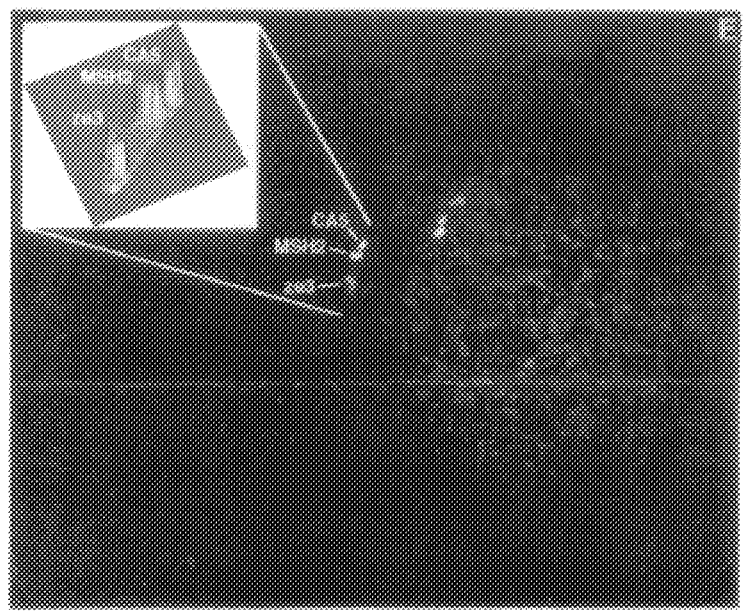

FIG. 5A

```
                                                                              Met Ala Val Gln Pro
-68  GG CGG GAA ACA GCT TAG TGG GTG TGG GGT CGC GCA TTT TCT TCA ACC AGG ACG TGA GGA GGT TTC GAC ATG GCG GTG CAG CCG

Lys Glu Thr Leu Gln Leu Glu Ser Ala Ala Glu Val Gly Phe Val Arg Phe Gln Gly Met Pro Glu Lys Pro Thr Thr
  6   AAG GAG ACG CTG CAG TTG GAG AGC GCG GCC GAG GTC GGC TTC CGC TTT CAG GGC ATG CCG GAG AAG CCG ACC ACC ACA
 16

Val Arg Leu Phe Asp Arg Gly Asp Phe Tyr Thr Ala His Gly Glu Asp Ala Leu Leu Ala Ala Arg Glu Val Phe Lys Thr Gln
 34   GTG CGC CTT TTC GAT CGG GGC GAC TTC TAT ACG GCG CAC GGC GAG GAC GCG CTG CTG GCC GCC CGG GAG GTG TTC AAG ACC CAG
100

Gly Val Ile Lys Tyr Met Gly Pro Ala Gly Ala Lys Asn Leu Gln Ser Val Val Leu Ser Lys Met Asn Phe Glu Ser Phe Val
 62   GGG GTG ATC AAG TAC ATG GGG CCG GCA GGA GCA AAG AAT CTG CAG AGT GTT GTG CTT AGT AAA ATG AAT TTT GAA TCT TTT GTA
184

Lys Asp Leu Leu Leu Val Arg Gln Tyr Arg Val Glu Val Tyr Lys Asn Arg Ala Gly Asn Lys Ala Ser Lys Glu Asn Asp Trp
 90   AAA GAT CTT CTT CTG GTT CGT CAG TAT AGA GTT GAA GTT TAT AAG AAT AGA GCA GGT AAT AAG GCA TCC AAG GAG AAT GAT TGG
268

Tyr Leu Ala Tyr Lys Ala Ser Pro Gly Asn Leu Ser Gln Phe Glu Asp Ile Leu Phe Gly Asn Asn Asp Met Ser Ala Ser Ile
118   TAT TTG GCA TAT AAG GCT TCT CCT GGC AAT CTC TCT CAG TTT GAA GAT ATT CTC TTT GGT AAC AAT GAT ATG TCA GCT TCC ATT
352

Gly Val Val Gly Val Lys Met Ser Ala Val Gly Val Arg Gly Tyr Val Asp Ser Ile Gln Ile Gly Pro Lys Glu Cys Val Leu
146   GGT GTT GTG GGT GTT AAA ATG TCC GCA GTT GGT GTA CGT GGT TAT GTG GAT TCC ATA CAG ATA GGA CCA AAG GAA TGT GTT TTA
436

Gly Leu Cys Glu Phe Pro Asp Asn Asp Gln Phe Ser Asn Leu Glu Ala Leu Leu Ile Gln Ile Gly Pro Lys Glu Cys Val Leu
174   GGA CTG TGT GAA TTC CCT GAT AAT GAT CAG TTC TCC AAT CTT GAG GCT CTC CTC ATC CAG ATT GGA CCA AAG GAA TGT GTT TTA
520

Pro Gly Gly Glu Thr Ala Gly Asp Met Gly Lys Leu Arg Gln Ile Ile Gln Arg Gly Gly Ile Leu Ile Thr Glu Arg Lys Lys
202   CCC GGA GGA GAG ACT GCT GGA GAC ATG GGG AAA CTG AGA CAG ATA ATT CAA AGA GGA GGA ATT CTG ATC ACA GAA AGA AAA AAA
604

Ala Asp Phe Ser Thr Lys Asp Ile Tyr Gln Leu Asn Ser Arg Leu Asp Ser Leu Leu Lys Gly Leu Gln Gln Met Asn Ser Ala Val
230   GCT GAC TTT TCC ACA AAA GAC ATT TAT CAG CTC AAC TCC CGG CTT GAC TCT TTG AAA AAG GGA CTG CAG CAG ATG AAT AGT GCT GTA
688

Leu Pro Glu Met Glu Asn Gln Val Ala Val Ser Ser Leu Ser Ala Val Ile Lys Phe Leu Glu Leu Leu Ser Asp Asp Ser Asn
258   TTG CCA GAA ATG GAG AAT CAG GTT GCA GTT TCA TCT CTG TCT GCG GTA ATC AAG TTT TTA GAA CTC TTA TCA GAT GAT AGT AAC
772

Phe Gly Gln Phe Glu Leu Thr Thr Phe Asp Phe Ser Gln Tyr Met Lys Leu Asp Ile Ala Ala Val Arg Ala Leu Asn Leu Phe
286   TTT GGA CAG TTT GAA CTG ACT ACT TTT GAC TTC AGC CAG TAT ATG AAA TTG GAT ATT GCA GCA GTC AGA GCC CTT AAC CTT TTT
856
```

FIG. 5B

| # | # | Codon sequence |
|---|---|---|
| 314 | 940 | Gln Gly Ser Val Glu Asp Thr Thr Gly Ser Gln Ser Leu Ala Ala Leu Leu Asn Lys Cys Lys Thr Pro Gln Gly Gln Arg Leu<br>CAG GGT TCT GTT GAA GAT ACC ACT GGC TCT CAG AGT CTG GCT GCC TTG CTG AAT AAG TGT AAA ACC CCT CAA GGA CAA AGA CTT |
| 342 | 1024 | Val Asn Gln Trp Ile Lys Gln Pro Leu Met Asp Lys Asn Arg Ile Glu Glu Arg Leu Asn Leu Val Glu Ala Phe Val Glu Asp<br>GTT AAC CAG TGG ATT AAG CAG CCT CTC ATG GAT AAG AAC AGA ATA GAG GAG AGA TTG AAT TTA GTG GAA GCT TTT GTA GAA GAT |
| 370 | 1108 | Ala Glu Leu Arg Gln Thr Leu Gln Glu Asp Leu Asp Arg Phe Pro Asp Leu Asn Arg Ala Lys Lys Phe Gln Arg Gln<br>GCA GAA TTG AGG CAG ACT TTA CAA GAA GAT CTT GAT CGA TTC CCA GAT CTT AAC CGA GCC AAG AAG TTT CAA AGA CAA |
| 398 | 1192 | Ala Ala Asn Leu Gln Asp Cys Tyr Arg Leu Tyr Ile Asp Gln Ile Gln Ala Leu Glu Lys His Glu<br>GCA GCA AAC TTA CAA GAT TGT CGA CTC TAT ATA CAA CTA CCT AAT GTT ATA CAG GCT CTG AAA AAA CAT GAA |
| 426 | 1276 | Gly Lys His Gln Lys Leu Leu Leu Ala Val Phe Val Thr Pro Leu Thr Asp Phe Ser Lys Phe Gln Glu Met<br>GGA AAA CAC CAG AAA TTA TTG GCA GTT TTT GTG ACT CCT CTT ACT GAT TTC TCC AAG TTT CAG GAA ATG |
| 454 | 1360 | Ile Glu Thr Thr Leu Asp Met Asn His Glu Phe Leu Val Lys Pro Asn Leu Ser Glu Leu<br>ATA GAA ACA ACT TTA GAT ATG AAT CAG GTG GAA AAC CAT GAA TTC CTT GTA AAA CCT TCA TTT GAT CCT AAT CTC AGT GAA TTA |
| 482 | 1444 | Arg Glu Ile Met Asn Asp Ile Ser Ala Ala Arg Asp Leu Gly Leu Asp Pro Gly Lys<br>AGA GAA ATA ATG AAT GAC TTG GAA AAG ATG CAG TCA ACA TTA ATA AGT GCA GCC AGA GAT CTT GGC TTG GAC CCT GGC AAA |
| 510 | 1528 | Gln Ile Lys Leu Asp Ser Ser Ala Gln Phe Gly Tyr Tyr Phe Arg Val Thr Cys Lys Glu Glu Lys Val Leu Arg Asn Asn Lys<br>CAG ATT AAA CTG GAT TCC AGT GCA CAG CAG TTT GGA TAT TAC TTT CGT GTA ACC TGT AAG GAA GAA AAA GTC CTT CGT AAC AAT AAA |
| 538 | 1612 | Asn Phe Ser Thr Val Asp Ile Gln Lys Asn Gly Val Lys Phe Thr Asn Ser Leu Thr Ser Leu Asn Glu Glu Tyr Thr Lys<br>AAC TTT AGT ACT GTA GAT ATC CAG AAG AAT GGT GTT AAA TTT ACC AAC AGC AAA TTG ACT TCT TTA AAT GAA GAG TAT ACC AAA |
| 566 | 1696 | Asn Lys Thr Glu Tyr Glu Ala Gln Ile Val Lys Val Ser Phe Ala His Val Val Ser Asn Gly Tyr Val Glu Pro Met Gln<br>AAT AAA ACA GAA TAT GAA GCC CAG ATT GTT AAA GTT TCT TTT GCT CAC GTG GTC AGC AAT GGT TAT GTT GAA CCA ATG CAG |
| 594 | 1780 | Thr Leu Asn Asp Val Leu Ile Gln Leu Leu Ala Val His Val Val Lys Asn Gly Ala Pro Val Pro Tyr Val Arg<br>ACA CTC AAT GAT GTG TTA GCT CAG CTA GCT GTT CAC GTG GTC AAT GGA GCA CCT GTT CCA TAT GTA CGA |
| 622 | 1864 | Pro Ala Ile Leu Glu Lys Gly Gln Gly Arg Ile Ile Leu Lys Ala Ser Arg His Ala Cys Val Gln Asp Glu Ile Ala<br>CCA GCC ATT TTG GAG AAA GGA CAA GGA AGA ATT ATA TTA AAA GCA TCC AGG CAT GCT TGT GTT CAA GAT GAA ATT GCA |

FIG. 5C

```
650  Phe Ile Pro Asn Asp Val Tyr Phe Glu Lys Asp Lys Gln Met Phe His Ile Ile Thr Gly Pro Asn Met Gly Gly Lys Ser Thr
1948 TTT ATT CCT AAT GAC GTA TAC TTT GAA AAA GAT AAA CAG ATG TTC CAC ATC ATT ACT GGC CCC AAT ATG GGA GGT AAA TCA ACA

678  Tyr Ile Arg Gln Thr Gly Val Ile Val Leu Met Ala Gln Ile Gly Cys Phe Val Pro Cys Glu Ser Ala Glu Val Ser Ile Val
2032 TAT ATT CGA CAA ACT GGG GTG ATA GTA CTC ATG GCC CAA ATT GGG TGT TTT GTG CCA TGT GAG TCA GCA GAA GTG TCC ATT GTG

706  Asp Cys Ile Leu Ala Arg Val Gly Ala Gly Asp Ser Gln Leu Lys Gly Val Ser Thr Phe Met Ala Glu Met Leu Glu Thr Ala
2116 GAC TGC ATC TTA GCC CGA GTA GGG GCT GGT GAC AGT CAA TTG AAA GGA GTC TCC ACG TTC ATG GCT GAA ATG TTG GAA ACT GCT

734  Ser Ile Leu Arg Ser Ala Thr Lys Asp Ser Leu Ile Ile Asp Glu Leu Gly Arg Gly Thr Ser Thr Tyr Asp Gly Phe Gly
2200 TCT ATC CTC AGG TCT GCA ACC AAA GAT TCA TTA ATA ATC GAT GAA TTA GGA AGA ACT TCT ACC TAC GAT GGA TTT GGG

762  Leu Ala Trp Ala Ile Ser Glu Tyr Ile Ala Thr Lys Ile Gly Ala Phe Cys Met Phe Ala Thr His Phe His Glu Leu Thr Ala
2284 TTA GCA TGG GCT ATA TCA GAA TAC ATT GCA ACA AAG ATT GGT GCT TTT TGC ATG TTT GCA ACC CAT TTT CAT GAA CTT ACT GCC

790  Leu Ala Asn Gln Ile Pro Thr Val Asn Asn Leu His Val Thr Ala Leu Thr Thr Glu Glu Thr Leu Thr Met Leu Tyr Gln Val
2368 TTG GCC AAT CAG ATA CCA ACT GTT AAT AAT CTA CAT GTC ACA GCA CTC ACC ACT GAA GAG ACT CTA ACT ATG CTT TAT CAG GTG

818  Lys Lys Gly Val Cys Asp Gln Ser Phe Gly Ile His Val Ala Glu Leu Ala Asn Phe Pro Lys His Val Ile Glu Cys Ala Lys
2452 AAG AAA GGT GTC TGT GAT CAA AGT TTT GGG ATT CAT GTT GCA GAG CTT GCT AAT TTC CCT AAG CAT GTA ATA GAG TGT GCT AAA

846  Gln Lys Ala Leu Glu Leu Glu Glu Phe Gln Tyr Ile Gly Glu Ser Gln Gly Tyr Asp Ile Met Glu Pro Ala Ala Lys Lys Cys
2536 CAG AAA GCC CTG GAA CTT GAA GAG TTT CAG TAT ATT GGA GAA TCG CAA GGA TAT GAT ATC ATG GAA CCA GCA GCA AAG AAG TGC

874  Tyr Leu Glu Arg Glu Thr Glu Lys Glu Val Ile Ile Gln Glu Phe Leu Ser Lys Val Lys Gln Met Pro Phe Thr Glu Met Ser Glu
2620 TAT CTG GAA AGA GAG ACA GAA AAG GAA GTA ATT ATT CAG GAG TTC CTG TCC AAG GTG AAA CAA ATG CCC TTT ACT GAA ATG TCA GAA

902  Glu Asn Ile Thr Ile Lys Leu Lys Gln Leu Lys Ala Glu Val Ile Ala Lys Asn Asn Ser Phe Val Asn Glu Ile Ile Ser Arg
2704 GAA AAC ATC ACA ATA AAG TTA AAA CAG CTA AAA GCT GAA GTA ATA GCA AAG AAT AAT AGC TTT GTA AAT GAA ATC ATT TCA CGA

930  Ile Lys Val Thr Thr
2788 ATA AAA GTT ACT ACG TGA AAA ATC CCA GTA ATG GAA TGA ACG TAA TAT TGA TAA GCT ATT GTC TGT AAT AGT TTT ATA TTG TTT

2872 TAT ATT AA
```

FIG. 6A

```
hMSH2   mavqpkstlqlesaafvgfvrffqgmrekpttvriffdrgdfyTahgedALLAaREvekagmikymgpagaknlqsvvl   80
yMSH2   msstrpelkfsdvseernfykytglpkkplkcpirievdkgdyytviesdRifvadshvhgslincqldpvtaknfhep   80 hMSH2   sknfesfvkdllamcqyrvgvyknragnkaskendmyiaykasegnlsfediifgfndsasigvvglkmsavdeeqrq   160
yMSH2   ekvtvslqvlatimkiclleigykveiy----dkgtikiksasrgnieqvnelanmnidssiilaslkiqwnsqdenci   156 hMSH2   vgvgvvdsiqrklglcefpndqfsnleallicigprecvl----pggelagdvgklrqiiqrggiltlerkkadlestid   236
yMSH2   igvafidtaykvelldivdnevisnleesfioglvmeglvqdltsnsnsnaevqkvinvidrcgcvulensefsekd   236 hMSH2   iyqdnrllkgkkgeqmnsavlppmenqvavsslsavikleliasdsnfsqfeltfdfsqyrlddiaavralnlpqgs   316
yMSH2   veldtrklgddlals-----lpqkysklsmgacnalgvlqlassedqvgkveivehklkefmkdasaikalnlpqg   311 hMSH2   vedttgsqslaa-----------------lankqckipqeqrlvnchikqpldtkkrieerlnievpafledaelrqiqed   379
yMSH2   pqnpfqsnneavsgftsagnsgkvtslfqllawhqkvnagvriilneivlkqpitnidetnkrhdavdyllidqielroitse   391 hMSH2   lirrfpelnrlakkfqraniqdcyrllqginqlenviqalekheqkhqk-----lllavfvtplidlrsdfskfqem   453
yMSH2   ylpmidirrltkklnkr-gnledvlkikqfskriqenvqvftsfleddsptepvneivrswlaplhhveplskfeem   470 hMSH2   ievilidmdqvenhe-flvrpsednlselreimndiekkmqstlisaardlglddpgkqikldssaqfgyyfrvckeekv   532
```

FIG. 6B

```
yMSH2  VETIVDLDAYEENNeFMIKVEENEELGKIRSKAETLRDEIHSIHLDSAEDLGFDPDKKLRLENHHLHEWCMQLRNDAKE    550
hMSH2  LRNNKNSTVDIQKNGVKEINSKLTSLNEEYTKNKTEYEEAQDAIVKEIVNISSGVEPMQTENDVLAQLENDAIVSFAHVS    612
yMSH2  LPKHKKQIELSTVKAGIFESTKQLKSIANETNILQKEYDKQQSALVREININLLTTPVFEKISLVIAHLDVIIASFAHTS    630
hMSH2  NGAPVPYVRPailekgqg-RIILKASRHACVEVQDEIAFIPNDVYFEKDKQMHIITGPNMGGKSTYIRQTGVIVLMAQI    691
yMSH2  SYAPIPYIRPklhpmdserRTHLISSRHPVLEAQDDISFISNDVTLESGKDELILTGPNMGGKSTYIRQVGVISLMAQI    710
hMSH2  GCFVPCESAEVSIVDCILARVGAGDSQLKGVSTFMADMLETASILRSATKDSLIIDELGRGTSTYDGFGLAWAISEYIA    771
yMSH2  GCFVPCEEAEIAIVDAILCRVGAGDSQLKGVSTFMVEILETASILKNASKNSLIIVDELGRGTSTYDGFGLAWAIABHIA    790
hMSH2  IRKIGAFCMFATHFHELALANQIPTVNMLHVTALtt------EETLTMLYQVKKGVCDQSFGIHVAELANFPKHVIE    842
yMSH2  SKIGCEALFATHFHELELSEKLENVKNMHVVAhieknlkeqkhdDEDITLLYKVEPGISDQSFGIHVAEVVQFPEKIVK    870
hMSH2  CAKQKALELEEFQYIGESggydiMepaakkcyleEeggekiiqeflsLvkqMpftemseEniEiklkElkaevlEknnsf    922
yMSH2  MAKRKANELEDLKTNNEDlkkakIslqevmegniElkallkewirkvMeegIhdpskitEeaSqhkiEellraIanepek    950
hMSH2  vMEiisrEkvEt----                                                                  934
yMSH2  enEmyleEykSpccyn                                                                  966
```

DIAGNOSTIC METHOD EMPLOYING MSH2 PROTEIN

This application is a division of application Ser. No. 08/160,295, Filed Dec. 2, 1993, now pending which is a continuation-in-part of Ser. No. 08/056,546, filed May 5, 1993 now U.S. Pat. No. 5,492,808.

This invention was made using U.S. government grants from the NIH CA47527, CA09320, GM26449, CA09243, CA41183, CA42705 CA57435, and CA35494, as well as grants from the Department of Energy DOE/ERN/F139 and DE-FG 09291ER-61139. Therefore the U.S. government retains certain rights to the invention.

TECHNICAL FIELD OF THE INVENTION

The invention relates to a gene which predisposes individuals to colorectal and other cancers. In addition, it also relates to biochemical tests which can be used to identify drugs for treatment of affected individuals.

BACKGROUND OF THE INVENTION

HNPCC (Lynch syndrome) is one of the most common cancer predisposition syndromes, affecting as many as 1 in 200 individuals in the western world (Lynch et al., 1993). Affected individuals develop tumors of the colon, endometrium, ovary and other organs, often before 50 years of age. Although the familial nature of this syndrome was discovered nearly a century ago (Warthin et al., 1913), the role of heredity in its causation remained difficult to define (Lynch et al., 1966). Recently, however, linkage analysis in two large kindreds demonstrated association with polymorphic markers on chromosome 2 (Peltomaki et al., 1993a). Studies in other families suggested that neoplasia in a major fraction of HNPCC kindreds is linked to this same chromosome 2p locus (Aaltonen et al., 1993).

HNPCC is defined clinically by the occurrence of early-onset colon and other specific cancers in first degree relatives spanning at least two generations (Lynch et al., 1993). The predisposition is inherited in an autosomal dominant fashion. It was initially expected that the gene(s) responsible for HNPCC was a tumor suppressor gene, as other previously characterized cancer predisposition syndromes with this mode of inheritance are caused by suppressor gene mutations (reviewed in Knudson, 1993). But the analysis of tumors from HNPCC patients suggested a different mechanism. Most loci encoding tumor suppressor genes undergo somatic losses during tumorigenesis (Stanbridge, 1990). In contrast, both alleles of chromosome 2p loci were found to be retained in HNPCC tumors (Aaltonen et al., 1993). During this search for chromosome 2 losses, however, it was noted that HNPCC tumors exhibited somatic alterations of numerous microsatellite sequences.

Widespread, subtle alterations of the cancer cell genome were first detected in a subset of sporadic colorectal tumors using the arbitrarily-primed polymerase chain reaction (Peinado et al., 1992). These alterations were subsequently found to represent deletions of up to 4 nucleotides in genomic polyA tracts (Ionov et al., 1993). Other studies showed that a similar, distinctive subgroup of sporadic tumors had insertions or deletions in a variety of simple repeated sequences, particularly microsatellite sequences consisting of dinucleotide or trinucleotide repeats (Ionov et al., 1993; Thibodeau et al., 1993; Aaltonen et al., 1993). Interestingly, these sporadic tumors had certain features in common with those developing in HNPCC kindreds, such as a tendency to be located on the right side of the colon and to be near-diploid. These and other data suggested that HNPCC and a subset of sporadic tumors were associated with a heritable defect causing replication errors (RER) of microsatellites (Ionov et al., 1993; Aaltonen et al., 1993).

The mechanism underlying the postulated defect could not be determined from the study of tumor DNA, but studies in simpler organisms provided an intriguing possibility (Levinson and Gutman, 1987; Strand et al., 1993). This work showed that bacteria and yeast containing defective mismatch repair genes manifest instability of dinucleotide repeats. The disruption of genes primarily involved in DNA replication or recombination had no apparent effect on the fidelity of microsatellite replication (reviewed in Kunkel, 1993). These pivotal studies suggested that defective mismatch repair might be responsible for the microsatellite alterations in the tumors from HNPCC patients (Strand et al., 1993).

Thus there is a need in the art to identify the actual gene and protein responsible for hereditary non-polyposis colorectal cancer and the replication error phenotype found in both hereditary and sporadic tumors. Identification of the gene and protein would allow more widespread diagnostic screening for hereditary non-polyposis colorectal cancer than is currently possible. Identification of the involved gene and protein would also enable the rational screening of compounds for use in drug therapy of hereditary non-polyposis colorectal cancer, and would enable gene therapy for affected individuals.

SUMMARY OF THE INVENTION

It is an object of the invention to provide a DNA molecule which when mutated is the genetic determinant for hereditary non-polyposis colorectal cancer.

It is another object of the invention to provide DNA molecules which contain specific mutations which cause hereditary non-polyposis colorectal cancer.

It is yet another object of the invention to provide methods of treating persons who are predisposed to hereditary non-polyposis colorectal cancer.

It is still another object of the invention to provide methods for determining a predisposition to cancer.

It is a further object of the invention to provide methods for screening test compounds to identify therapeutic agents for treating persons predisposed to hereditary non-polyposis colorectal cancer.

It is still another object of the invention to provide a protein which is important for human DNA mismatch repair.

It is yet another object of the invention to provide a transgenic animal for studying potential therapies for hereditary non-polyposis colorectal cancer.

These and other objects of the invention are provided by one or more of the embodiments described below. In one embodiment of the invention an isolated and purified DNA molecule is provided. The molecule has a sequence of at least about 20 nucleotides of hMSH2, as shown in SEQ ID NO:1.

In another embodiment of the invention an isolated and purified DNA molecule is provided. The DNA molecule has a sequence of at least about 20 nucleotides of an hMSH2 allele found in a tumor wherein said DNA molecule contains a mutation relative to hMSH2 shown in SEQ ID NO:1.

In yet another embodiment of the invention a method of treating a person predisposed to hereditary non-polyposis colorectal cancer is provided. The method prevents accumulation of somatic mutations. The method involves administering a DNA molecule which has a sequence of at least about 20 nucleotides of hMSH2, as shown in SEQ ID NO:1, to a person having a mutation in an hMSH2 allele which predisposes the person to hereditary non-polyposis colorectal cancer, wherein said DNA molecule is sufficient to remedy the mutation in an hMSH2 allele of the person.

In another embodiment of the invention a method is provided for determining a predisposition to cancer. The method involves testing a body sample of a human to ascertain the presence of a mutation in hMSH2 which affects hMSH2 expression or hMSH2 protein function, the presence of such a mutation indicating a predisposition to cancer.

In still another embodiment of the invention a method is provided for screening to identify therapeutic agents which can prevent or ameliorate tumors. The screening method involves contacting a test compound with a purified hMSH2 protein or a cell; determining the ability of the hMSH2 protein or the cell to perform DNA mismatch repair, a test compound which increases the ability of said hMSH2 protein or said cell to perform DNA mismatch repair being a potential therapeutic agent.

In another embodiment of the invention an isolated and purified protein is provided. The protein has the sequence shown in SEQ ID NO:2.

In still another embodiment of the invention a transgenic animal is provided. The transgenic (nonhuman) animal maintains an hMSH2 allele in its germline. The hMSH2 allele is one which is found in humans having hereditary non-polyposis colorectal cancer or in RER$^+$ tumors. Also provided are animals which have no wild-type MSH2 alleles, due to mutations introduced.

Thus the present invention provides the art with the sequence of the gene responsible for hereditary non-polyposis colorectal cancer and information regarding the mechanism by which it causes tumors. This enables the art to practice a variety of techniques to identify persons at risk of developing a variety of cancers and to treat them to prevent such cancers from actually developing.

PCR was used to determine whether each of the listed markers was present (black box) or absent (white box) in the indicated hybrid. The laboratory name of each hybrid and the formal name (in parentheses) is listed. The hybrid panel was also validated with ten additional polymorphic markers outside of the 136–177 region. M: hybrid derived from microcell-mediated chromosome 2 transfer; T: derived from t(X;2) translocation; X: derived from X-irradiated chromosome 2 donor. MO: mouse-human hybrid; HA: hamster-human hybrid; RA: rat-human hybrid; TEL: telomere; CEN: centromere.

FIG. 2 shows a FISH analysis which was used to determine the proximity and ordering of DNA sequences within chromosome band 2p16.

Panels 2A and 2B show FISH mapping of the 123 marker. Panel 2A shows G-banded metaphase chromosome 2. Panel 2B shows identical chromosome as in Panel 2A following FISH with a biotin-labeled P1 clone for the 123 marker. Results localize the 123 marker to chromosome band 2p16.3. Panels 2C and 2D show co-hybridization documenting the coincident localization of a microdissection (Micro-FISH) probe from chromosome 2p16 and the 123 marker. Panel 2C shows DAPI stained metaphase chromosome 2. Panel 2D shows simultaneous hybridization of the biotin-labeled 123 probe (appearing as an intensely staining smaller circle) and the Spectrum-Orange labeled 2p16 Micro-FISH probe (appearing as a diffusely staining larger circle). Panel 2E shows a representative example of an interphase nucleus simultaneously hybridized with P1 clones for CA5, hMSH2 and ze3. The results were used to directly measure the distances between markers in order to establish the order and relative distance between markers (after Trask et al., 1989). Inset: The image processing program NIH Image was used to provide an average gray value displayed as a surface plot to support the length measurements and to graphically illustrate the relative order information. The surface plot presented defines the specified interphase chromosome and the relative order CA-MSH2-ze3.

Figure 3:
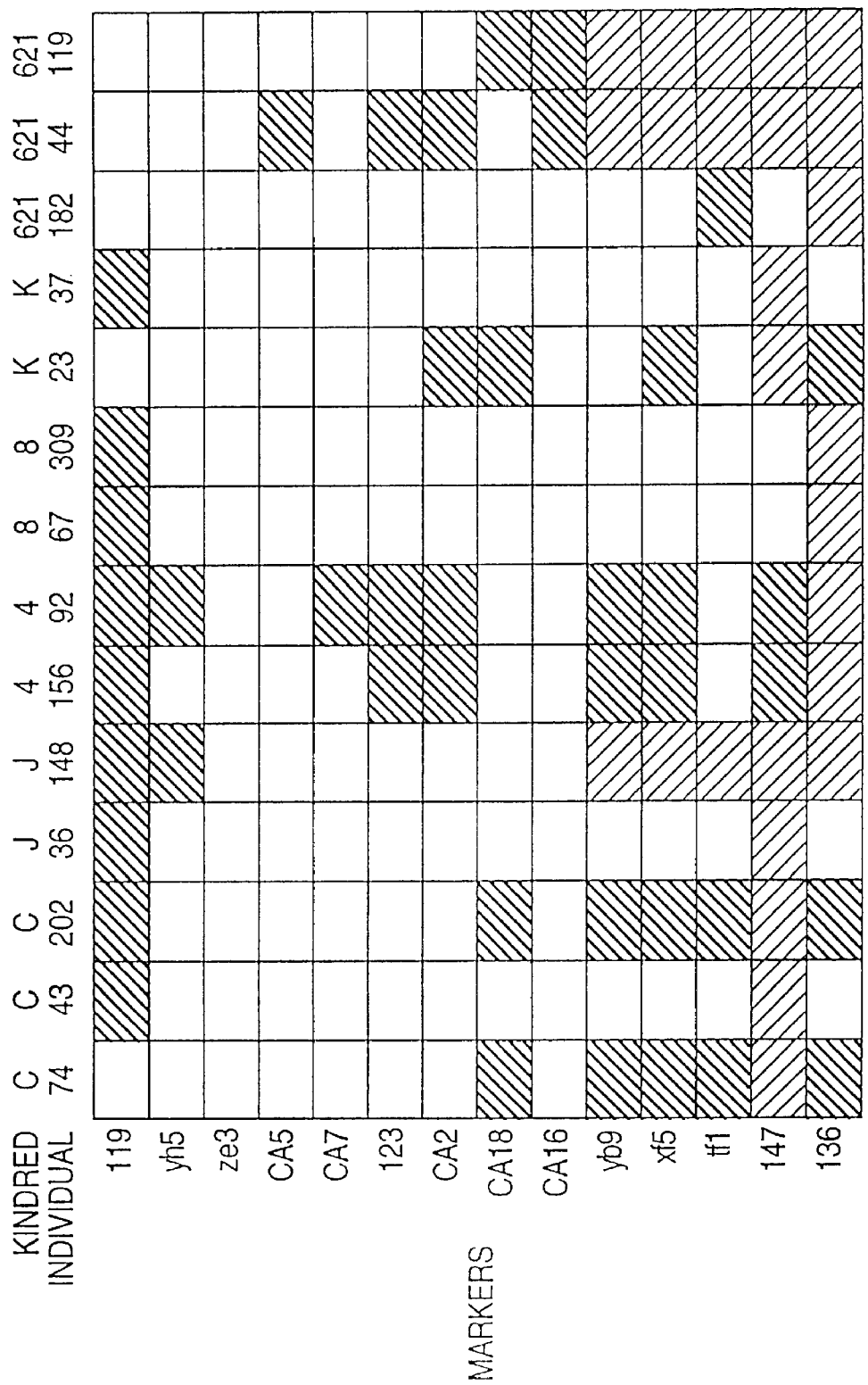
Figure 4A:
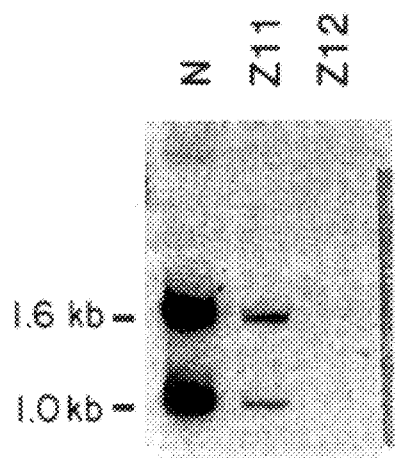
Figure 4B:
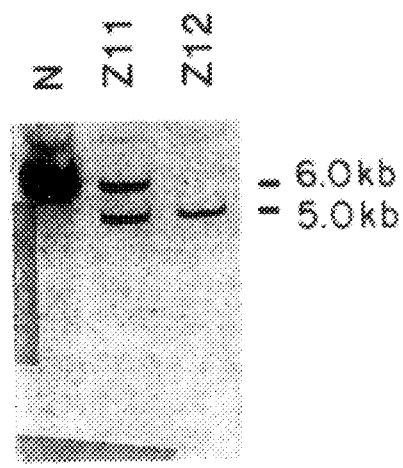
Figure 4C:
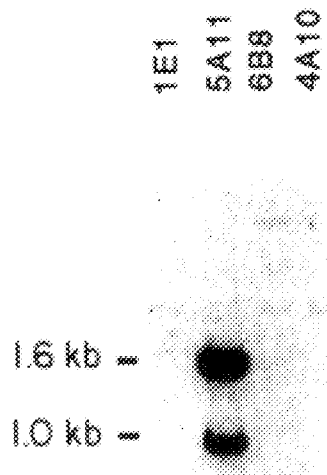
Figure 4D:
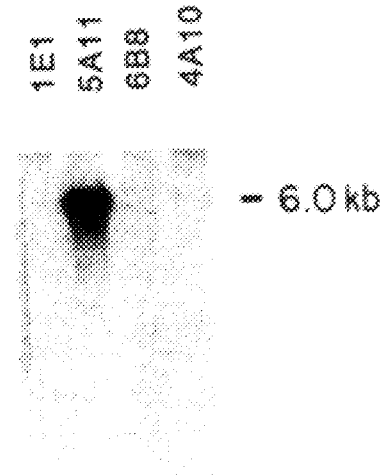

FIG. 3 shows linkage analysis of HNPCC pedigrees.

All affected individuals in which meiotic recombination occurred between markers 119 and 136 are included. A black box indicates that the individual did not contain the allele associated with disease in his/her family or that the individual inherited an allele not associated with disease from his/her affected parent. A white box indicates that the individual had an allele which was the same size as the disease-associated allele. A hatched circle indicates that the marker was not studied. All individuals had colon or endometrial cancer at less than 55 years of age, or had progeny with such disease but did not indicate that the patient necessarily had disease-associated alleles because phase could usually not be determined.

FIG. 4 shows hMSH2 gene localization.

Southern blots containing EcoRI (FIGS. 4A and 4C) and PstI (FIGS. 4B and 4D) digested DNA from the indicated somatic cell hybrids (FIGS. 4A and 4B) or YAC clones (FIGS. 4C and 4D) were hybridized with a radiolabelled insert from cDNA clone pNP-23. Southern blotting and hybridization were performed as described (Vogelstein et al., 1987). Autoradiographs are shown. The 5.0 kb PstI fragment in hybrids Z11 and Z12 is derived from hamster DNA.

FIG. 5 shows the cDNA sequence of hMSH2.

An open reading frame (ORF) begins at nucleotide 1 and ends at nt 2802. The predicted amino acid sequence is shown. The sequence downstream of nt 2879 was not determined.

FIG. 6 shows homology between yeast and human MSH2 genes.

The predicted amino acid sequences of yeast (y) MSH2 (Reenan and Kolodner, 1992) and human MSH2 genes are compared within the region of highest homology. Blocks of similar amino acids are shaded.

FIG. 7 shows germline and somatic mutations of hMSH2.

Figures 7A, 7B, 7C:
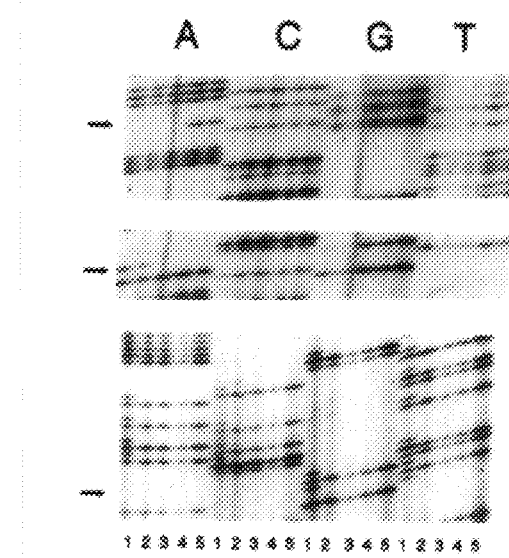

Autoradiographs of polyacrylamide gels containing the sequencing reactions derived from PCR products are shown. The 1.4 kb PCR products containing a conserved region of hMSH2 were generated from genomic DNA samples as described in the Examples. Antisense primers were used in the sequencing reactions. The ddA mixes from each sequencing reaction were loaded in adjacent lanes to facilitate comparison, as were those for C, G, and T. The DNA samples were derived from the tumor (lane 1) and normal colon (lane 2) of patient Cx10, an RER-colon tumor cell line (lane 3), and lymphocytes of patients J-42 (lane 4) and J-143 (lane 5). FIG. 7A: A transition (C to T at codon 622) in lymphocyte DNA can be observed in HNPCC patients J42 and J-143. FIG. 7B: A transition (C to T at nt codon 639) in tumor (lane 1) and normal colonic mucosa (lane 2) of patient Cx10. FIG. 7C: A substitution of a TG dinucleotide for an A at codon 663 can be observed in DNA of the tumor of patient Cx10, (lane 1), but not in DNA from her normal colon (lane 2). Arrows mark the substitutions in panel A and B and the TG dinucleotide insertion site in panel C.

DETAILED DESCRIPTION OF THE PREFERRED EMBODIMENTS

The disclosure of Ser. No. 08/056,546, filed May 5, 1993, is expressly incorporated herein.

It is a discovery of the present invention that the gene responsible for hereditary non-polyposis colorectal cancer is hMSH2, a human analog of bacterial MutS. The cDNA sequence of hMSH2 is shown in SEQ ID NO:1. This gene encodes a DNA mismatch repair enzyme. Mutation of the gene causes cells to accumulate mutations. For example, the observed replication error phenotype (RER$^+$) found in both sporadic and hereditary non-polyposis colorectal cancer consists of variations (insertions and deletions) in microsatellite DNA. In yeast and bacteria defective MutS-related genes cause other types of mutations as well.

Useful DNA molecules according to the invention are those which will specifically hybridize to hMSH2 sequences. Typically these are at least about 20 nucleotides in length and have the nucleotide sequence as shown in SEQ ID NO:1. Such molecules can be labeled, according to any technique known in the art, such as with radiolabels, fluorescent labels, enzymatic labels, sequence tags, etc. According to another aspect of the invention, the DNA molecules contain a mutation which has been found in tumors of HNPCC patients or in sporadic RER$^+$ tumors. Such molecules can be used as allele-specific oligonucleotide probes to track a particular mutation through a family.

According to some aspects of the invention, it is desirable that the DNA encode all or a part of the hMSH2 protein as shown in SEQ ID NO:2. To obtain expression of the protein the DNA sequence can be operably linked to appropriate control sequences, such as promotor, Kozak consensus, and terminator sequences.

A person who is predisposed to develop cancers due to inheritance of a mutant hMSH2 allele can be treated by administration of a DNA molecule which contains all or a part of the normal hMSH2 gene sequence as shown in SEQ ID NO:1. A portion of the gene sequence will be useful when it spans the location of the mutation which is present in the mutant allele, so that a double recombination event between the mutant allele and the normal portion "corrects" the defect present in the person. A portion of the gene can also be usefully administered when it encodes enough of the protein to express a functional DNA mismatch repair enzyme. Such a portion need not necessarily recombine with the mutant allele, but can be maintained at a separate locus in the genome or on an independently replicating vector.

Means for administering DNA to humans are known in the art, and any can be used as is convenient. A variety of vectors are also known for this purpose. According to some techniques vectors are not required. Such techniques are well known to those of skill in the art.

Also contemplated as part of the present invention is the use of a combined anti-neoplastic therapy regimen. Such a combined regimen is useful for patients having an RER$^+$ tumor, whether sporadic or associated with HNPCC. The regimen combines any standard anti-neoplastic therapy to which a patient can become resistant and hMSH2 gene therapy, as described above. By remedying the defect present in RER$^+$ cells, i.e., an hMSH2 mutation, the likelihood of the tumor developing a resistance mutation is greatly diminished. By delaying or preventing the onset of resistance, the life of cancer patients can be prolonged. In addition, such prevention of resistance allows a greater degree of tumor destruction by the therapeutic agent. Examples of anti-neoplastic therapies which can be combined with hMSH2 gene therapy are hormones, radiation, cytotoxic drugs, cytotoxins, and antibodies.

Body samples can be tested to determine whether the hMSH2 gene is normal or mutant. Mutations are those deviations from the sequence shown in SEQ ID NO:1 which are associated with disease and which cause a change in hMSH2 protein function or expression. Such mutations include nonconservative amino acid substitutions, deletions, premature terminations and frameshifts. See Table I. Suitable body samples for testing include those comprising DNA, RNA, or protein, obtained from biopsies, blood, prenatal, or embryonic tissues, for example. P Provided with the information that the defect causing HNPCC and sporadic RER$^+$ tumors is in a DNA mismatch repair enzyme, one can perform assays on test compounds and compositions to determine if they will remedy the defect. Such therapeutic compounds could bind to missense hMSH mutant proteins to restore the proteins to the normal, active conformation. Alternatively such therapeutic compounds could stimulate the expression of alternate pathways for mismatch repair. Screening for such therapeutic compounds could be performed by contacting test compounds with cells, either normal or those with an hMSH2 mutation found in a tumor. The ability of the cells which were contacted with the test compounds is compared with the ability of the same cells which were not contacted for mismatch repair activity. Such activity can be tested as is known in the art. See, for example, Levinson and Gutman, 1987, and Strand et al., 1993. Observation of changes in microsatellite DNA in cells is one way of assessing mismatch repair activity. Another approach is to assay DNA mismatch repair in vitro in nuclear extracts. See Holmes, 1990; Thomas, 1991; and Fang, 1993.

TABLE I

| Sample | Source | Type | Codon | cDNA Nucleotide Change | Predicted Coding Change |
|---|---|---|---|---|---|
| Family J | HNPCC Kindred | Germline | 622 | CCA to CTA | Pro to Leu |
| Family C | HNPCC Kindred | Germline | 265–314 | 793 to 942 Deletion | Inframe Deletion |
| Family 8 | HNPCC Kindred | Germline | 406 | CGA to TGA | Arg to Stop |
| Cx10 | RER + Tumor | Germline | 639 | CAT to TAT | His to Tyr |
|  |  | Somatic | 663 | ATG to TGTG | Frameshift |

Provided with the cDNA sequence and the amino acid sequence of hMSH2 protein, one of ordinary skill in the art can readily produce hMSH2 protein, isolated and purified from other human proteins. For example, recombinant cells or organisms can be used to produce the protein in bacteria, yeast, or other convenient cell system. The isolated and purified protein can be used in screening for new therapeutic agents, for example, in in vitro assays of DNA mismatch repair. The protein can also be used to raise antibodies against hMSH2. Therapeutic administration of the protein is also contemplated.

Transgenic animals are also contemplated by the present invention. These animals would have inserted in their germline hMSH2 alleles which are associated with HNPCC or sporadic tumors. Such animals could provide model systems for testing drugs and other therapeutic agents to prevent or retard the development of tumors. Also contemplated are genetically engineered animals which contain one or more mutations in their own MSH2 genes. The mutations will be engineered to correspond to mutations found in hMSH2 alleles which are found in HNPCC-affected individuals or in other human RER+ tumors. Animals with both native MSH2 alleles inactivated and containing a human wild-type or mutant hMSH2 allele are particularly desirable.

EXAMPLES

Example 1

Somatic Cell Hybrids

Figure 1:
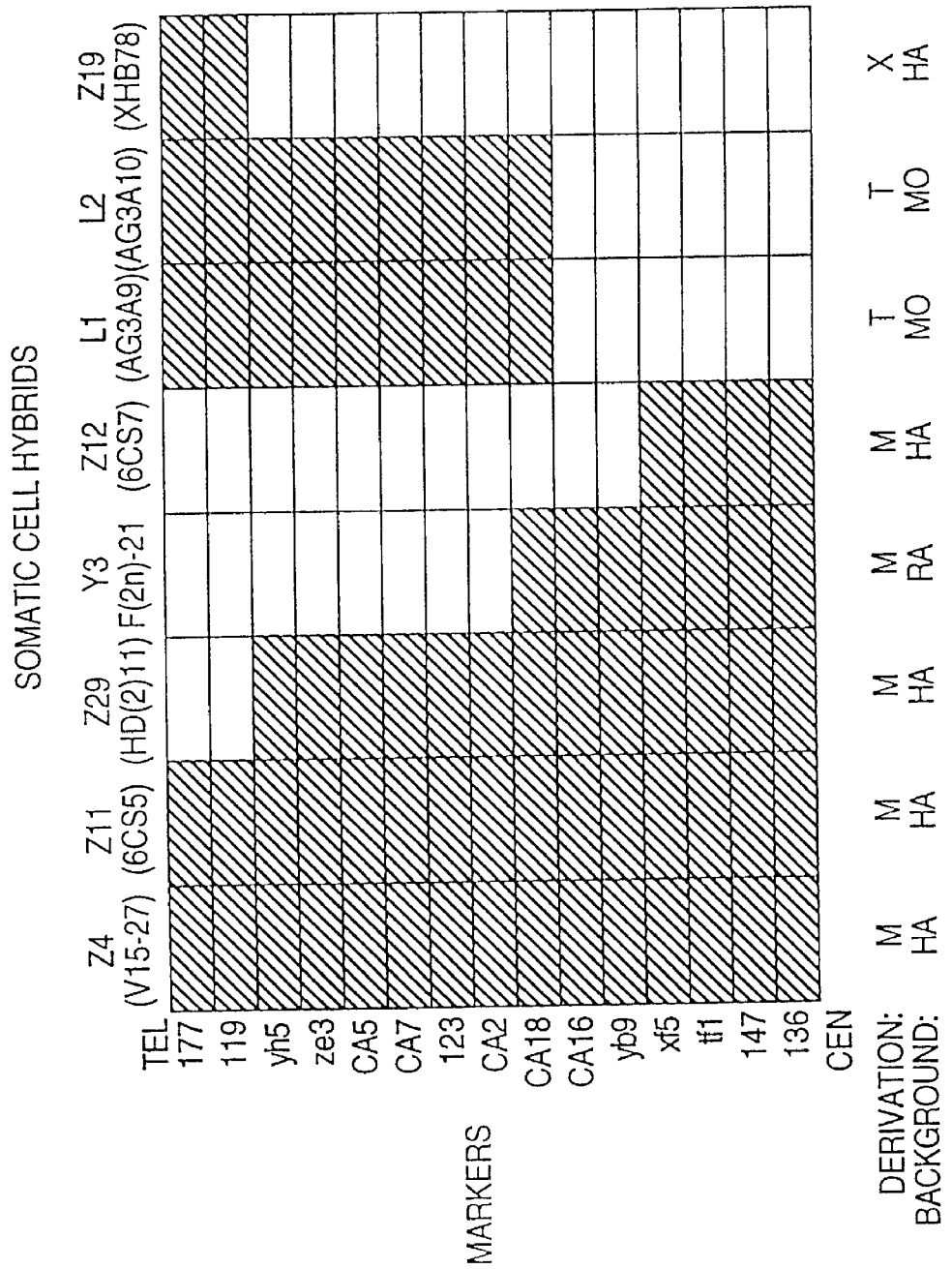
FIG. 1 summarizes the markers retained in somatic cell hybrids used in locating the hMSH2 gene.

A panel of human-hamster, human-mouse, and human-rat hybrid cell lines was developed to facilitate HNPCC mapping. Hybrids containing only portions of chromosome 2 were obtained by microcell-mediated chromosome transfer or by standard cell fusions following X-irradiation of the chromosome 2 donor. Additionally, two hybrids were used which contained a (X;2)(q28;p21) translocation derived from human fibroblasts. In previous studies, the HNPCC locus was mapped to the 25 cM region surrounding marker 123 and bordered by markers 119 and 136 (Peltomaki et al., 1993a). Thirty-eight hybrids were screened with these three chromosome 2p markers. Eight of the hybrids proved useful for mapping the relevant portion of chromosome 2p. For example, hybrids L1 and L2 contained the distal half of the region, including marker 123, while hybrid y3 contained the half proximal to marker 123 (FIG. 1).

Methods

Methods for the derivation of microcell-mediated chromosome 2 hybrids have been described previously (Chen et al., 1992; Spurr et al., 1993). Some hybrids were generated following fusion of X-irradiated donor cells containing human chromosome 2 to CHO cells (Chen et al., 1994). Mouse hybrids were derived by fusing HPRT deficient L cells (A9) with human fibroblasts (GM7503) containing a t(X;2)(q28,p21) translocation and selecting in media containing HAT.

Example 2

Polymorphic Markers

To map more finely the HNPCC locus, additional polymorphic markers were obtained in three ways. First, a genomic clone containing 85 kb surrounding the 123 marker was used for fluorescence in situ hybridization (FISH) to localize it to chromosomal band 2p16.3 (FIGS. 2A, B). The 2p16 band region was then microdissected, and the sequences within this band were amplified using the polymerase chain reaction and subcloned into plasmid vectors (see Experimental Procedures). The accuracy of the microdissection was confirmed using dual-color FISH by simultaneously hybridizing to microdissected material and a genomic clone containing marker 123 (FIGS. 2C, D). The subclones were screened by hybridization to a $(CA)_{15}$ probe, and hybridizing clones identified and sequenced. These sequences were then used to design oligonucleotide primers for PCR analysis of genomic DNA. Nineteen $(CA)_n$ repeat markers were identified in this way. Of these, four were highly polymorphic and mapped to the region between markers 119 and 136, as assessed by the somatic cell hybrid panel exhibited in FIG. 1. Second, eight additional $(CA)_n$ markers, cloned randomly from human genomic DNA using a poly (CA) probe, were found to lie between markers 119 and 136 by linkage analysis in CEPH pedigrees. Five of these were particularly informative and were used in our subsequent studies. Finally, one additional marker was identified by screening subclones of a genomic P1 clone containing marker 123 with a $(CA)_{15}$ probe. Through these analyses, thirteen new polymorphic markers were identified in the 25 cM interval between markers 119 and 136, resulting in an average marker spacing of ~2 cM (Table II). These markers were mapped with respect to one another by linkage in CEPH and HNPCC pedigrees as well as by analysis of somatic cell hybrids. These two mapping techniques provided consistent and complementary information. For example, the relative positions of CA16 and CA18 could not be distinguished through linkage analysis but could be determined with the somatic cell hybrids L1, L2, and Y3. Conversely, the relative position of the ze3 and yh5 markers could not be determined through somatic cell hybrid mapping, but could be discerned by linkage analysis.

TABLE II

| MARKER | DERIVATION | CM | LOD | HETEROZYGOSITY | YAC CLONES | P1 CLONES |
|---|---|---|---|---|---|---|
| 177 (AFM267zc9) | T | — | | 0.84 | | |
| 119 (AFM077yb7) | T | 6.1 | 5.5 | 0.77 | 11E1 | 406 |
| yh5 (AFM337yh5) | T | 6.4 | 15.4 | 0.76 | 4F4, 1E1 | 838, 839, 840 |
| ze3 (AFM200ze3) | T | 0.0 | — | 0.61 | 4F4, 1E1, 9H6, 4A10 | 836, 837 |
| CA5 (CA5) | M | 2.1 | 4.7 | 0.77 | 7F10, 4E2, 5A11 | 820 |
| CA7 (CA7) | M | 1.7 | 3 | 0.78 | 6B8 | |
| 123 (AFM093xh3) | T | 2.4 | 9.9 | 0.76 | 3D11, 8C7 | 210, 211 |
| CA2 (CA2) | P | 0.0 | — | 0.75 | 3D11, 8C7 | 210, 211 |
| CA18 (CA18) | M | 4.3 | 17.1 | 0.71 | 8E5 | |
| CA16 (CA16) | M | 0.0 | — | 0.69 | 8E5 | |
| yb9 (AFM320yb9) | T | 1.1 | 3.9 | 0.80 | 264 | |
| xf5 (AFM310xf5) | T | 2.7 | 17.6 | 0.76 | | |

TABLE II-continued

| MARKER | DERIVATION | CM | LOD | HETEROZYGOSITY | YAC CLONES | P1 CLONES |
|---|---|---|---|---|---|---|
| xf1 (AFM348tf1) | T | 0.0 | — | 0.79 | | |
| 147 (AFM199vb6) | T | 2.6 | 9.8 | 0.73 | | |
| 136 (AFM172xe7) | T | 2 | | 0.13 | | |
| 134 (AFM 168xg11) | T | 1 | | 0.76 | | 387, 388, 389 |

Methods

All markers were obtained by screening human genomic libraries with radiolabelled $(CA)_n$ probes (Weber and May, 1989). The "T" markers (see Table II) were generated from a library made from total human genomic DNA, as described in Weissenbach et al., 1992. The "M" markers were made from libraries generated from microdissected chromosome 2p16, as described below. The CA2 marker was generated from a library made from P1 clone 210 digested to completion with Sau3 and cloned into the XhoI site of lambda YES (Elledge et al., 1991). The sequences of the clones obtained from these libraries were determined, and primers surrounding the CA repeats chosen. Only primers giving robust amplification and high heterozygosity were used for detailed analysis of HNPCC kindreds. All markers used in this study were shown to be derived from chromosome 2p by both linkage analysis in the CEPH pedigrees and evaluation in the somatic cell hybrid panel shown in FIG. 1. The sequences of the primers and other details specific for each marker have been deposited with the Genome Data Base. Linkage analyses to obtain the map of the marker loci in CEPH families 1331, 1332, 1347, 1362, 1413, 1416, 884, and 102 (Weissenbach et al., 1992) were performed using the CLINK program of the LINKAGE program package (Lathrop et al., 1984) with the no sex difference option and 11-point computations. The odds for the best locus order supported by the data were evaluated against pairwise inversions of the loci.

Example 3

Genomic Clones

Many of the polymorphic markers shown in Table II were used to derive genomic clones containing 2p16 sequences. Genomic clones were obtained by PCR screening of human P1 and YAC libraries with these polymorphic markers, with ten additional sequence tagged sites (STS) derived from chromosome 2p16 microdissection, or with YAC junctions. Twenty-three P1 clones, each containing 85–95 kb, were obtained, as well as 35 YAC clones, containing 300 to 1800 kb. The YAC clones in some cases confirmed the linkage and somatic cell hybrid maps. For example, markers ze3 and yh5 were both found in YAC's 4F4 and 1E1 while CA16 and CA18 were both found in YAC 8E5, documenting their proximity. The highest density of genomic clones (28 YAC and 17 P1clones) was obtained between markers yb9 and yh5 (Table II), which became the region most likely to contain the HNPCC gene during the course of these studies. The region between yh5 and yb9 was predicted to contain ~9 Mb (assuming 1 Mb/per cM). Based on the sizes of the YAC clones, and taking into account their chimerism, we estimated that they contained over 70% of the sequences between yh5 and yb9.

Methods

The markers described in Table II were used to screen YAC or P1 libraries by PCR. The CEPH A library was obtained from Research Genetics, Inc. and consisted of 21,000 YAC clones, arrayed in a format allowing facile screening and unambiguous identification of positive clones. The sizes of ten of the YAC clones containing markers were determined by transverse alternating pulse-field gel electrophoresis using a GeneLine II apparatus from Beckman and found to average 0.7 Mb (range 0.2–1.8 Mb). In some cases, inverse PCR was used to determine the YAC junctions (Joslyn et al., 1991), and the derived sequence used for "chromosome walking" with the YAC or P1 libraries. The junctions were also used to design primers to test whether the ends of the YAC clones could be localized to chromosome 2p16 (and therefore presumably be non-chimeric). Three of four YAC clones which were tested in this way had both ends within the expected region of chromosome 2, as judged by analysis with the somatic cell hybrid panel. The human genomic P1 library was also screened by PCR (Genome Systems, Inc.). P1 clones M1015 and M1016, containing the hMSH2 gene, were used to determine intron-exon borders using sequencing primers from the exons and SequiTherm™ polymerase (Epicentre Technologies).

Example 4

Analysis of HNPCC Families

The markers described in Table II were then used to analyze six large HNPCC kindreds previously linked to chromosome 2p (Peltomaki et al., 1993a). Two hundred thirteen individuals, including 56 members affected with colorectal or endometrial cancer, were examined. Four of the kindreds were from the United States, one from Newfoundland and one from New Zealand. To increase the number of affected individuals that could be examined, we obtained formalin-fixed, paraffin-embedded sections of normal tissues from deceased individuals and purified DNA from them (Goelz et al., 1985a). A single allele of each of the thirteen markers was found to segregate with disease in each of the six families (i.e., the allele was found in over 50% of affected individuals). No allele of any marker was shared among the affected members of more than three kindreds.

Fourteen of the affected members contained only a subset of the expected alleles and therefore had undergone recombination between markers 119 and 136. Eleven of these individuals appeared to have simple, single recombination events. The most informative of these was in individual 148 from the J kindred and individual 44 from kindred 621 (FIG. 3). Individual 621–44 apparently retained the disease linked allele at markers distal to CA5, while demonstrating multiple recombinants at more proximal loci, thus placing the CA5 marker at the proximal border of the HNPCC locus. Individual J-148 apparently retained the disease-linked allele at all markers proximal to yh5, while exhibiting recombinants at yh5 and 119, thus placing the distal border at yh5. Assuming that the same gene was involved in both the J and 621 kindreds, the HNPCC gene was predicted to reside between markers CA5 and yh5, an area spanning approximately 2 cM (Table II).

The DNA of three affected individuals (C-202, 4-156, 4-92) appeared to have undergone two recombinations in the area. There was probably one recombinant per generation, and this could be demonstrated in C-202 by analysis of DNA from his parents; in the other cases, parental DNA was not available. All three individuals retained disease-linked alleles at CA5 and ze3 but not at more proximal and distal loci (FIG. 3). Combined with the data from the patients with single recombinations, the double recombinants suggested that the HNPCC gene resided between CA5 and ze3, a distance spanning less than 2 cM.

To determine the physical distances separating CA5, ze3, and yh5, metaphase and interphase FISH analysis was carried out. Dual-color FISH with P1 clones containing these markers was performed with P1 clones 820 and 838 (containing the markers CA5 and yh5, respectively) labeled with biotin and detected with fluorescein-labelled avidin, and clone 836 (containing marker ze3) labelled with Spectrum-Orange (Meltzer et al., 1992). The hybridization signals of these markers appeared coincident on metaphase chromosomes, confirming that they resided within an interval of <1.0 Mb. When FISH was performed on interphase nuclei, the relative positions of the three markers could be determined and the distances between them estimated (Trask et al., 1989). The results confirmed that the orientation of the markers was telomere-yh5-ze3-CA5-centromere (data not shown). Direct measurement of the distance between yh5 and ze3 was estimated at <0.3 Mb, consistent with the presence of both of these markers on YAC clones 4E4 and 1E1. Measurements of 48 interphase chromosomes provided an estimate of the distance between ze3 and CA5 at <0.8 Mb, independently confirming the linkage data.

Methods

G-banded metaphase chromosomes were microdissected with glass microneedles and amplified by PCR as previously described (Guan et al., 1993 Kao and Yu, 1991). For dual-color FISH, the PCR product was fluorochrome labelled (Spectrum-Orange, Imagenetics, Naperville, Ill.) or biotinylated in a secondary PCR reaction. P1 clones were labelled by nick-translation or by degenerate oligonucleotide primers (Guan et al., 1993). FISH was carried out as previously described (Guan et al., 1993) and visualized with a Zeiss Axiophot equipped with a dual-bandpass filter. For analysis of interphase FISH patterns, the distance between hybridization signals was measured in a minimum of 24 nuclei (Trask et al., 1989).

Example 5

Candidate Genes

On the basis of the mapping results described above, we could determine whether a given gene was a candidate for HNPCC by determining its position relative to the CA5-ze3 domain. The first gene considered was a human homolog of the Drosophila SOS gene (reviewed by Egan and Weinberg, 1993). This gene transmits signals from membrane bound receptors to the ras pathway in diverse eukaryotes. It was considered a candidate because another ras-interacting gene, NF1, causes a cancer predisposition syndrome (Viskochil et al., 1990; Wallace et al., 1990), and SOS has been localized to chromosome 2p16-21 by in situ hybridization (Webb et al., 1993). Using PCR to amplify SOS sequences from the hybrid panel, however, SOS was found to be distal to the CA5-yh5 domain (present in hybrid Z19 but not Z29).

We next examined the interferon-inducible RNA activated protein kinase gene PKR. This gene has been shown to have tumor suppressor ability (reviewed by Lengyel, 1993) and to map close to 2p16 (Hanash et al., 1993). We could not initially exclude PKR from the HNPCC domain, and therefore determined the sequence of its coding region in two individuals from HNPCC kindred C. Reverse transcriptase was used to generate cDNA from lymphoblastoid derived RNA of these two individuals, and PCR performed with primers specific for PKR. The PKR products were sequenced, and no deviations from the published sequence was identified within the coding region (Meurs et al., 1990). Subsequent studies showed that the PKR gene was distal to the yh5 marker, and thus could be excluded as a basis for HNPCC.

We then considered human homologs of the MutL and MutS mismatch repair genes previously shown to produce microsatellite instability in bacteria and yeast when disrupted (Levinson and Gutman, 1987; Strand et al., 1993). A human homolog of the yeast MutL-related gene PMS1 (Kramer et al., 1989) does not appear to reside on chromosome 2p (M. Liskay, personal communication). To identify homologs of MutS, we used degenerate oligonucleotide primers to PCR-amplify cDNA from colon cancer cell lines. The same primers had been previously used to identify the yeast MSH2 gene on the basis of its MutS homology (Reenan and Kolodner, 1992). Under non-stringent conditions of PCR, a fragment of the expected size was obtained and these fragments were cloned into plasmid vectors. Most of the clones contained ribosomal RNA genes, representing abundant transcripts with weak homology to the degenerate primers. A subset of the clones, however, contained sequences similar to that of the yeast MSH2 gene, and one such clone, pNP-23, was evaluated further. The human gene from which this clone is derived is hereafter referred to as hMSH2.

The insert from clone pNP-23 was used as a probe in Southern blots of somatic cell hybrid DNA. This insert hybridized to one or two fragments in human genomic DNA digested with PstI or EcoRI, respectively, and these fragments were present in hybrid Z30, containing most of human chromosome 2p. Analysis of other hybrids showed that the fragment was present in hybrids Z11, Z29, L1 and L2, but not Z12, Y3 or Z19, thereby localizing the human MSH2 (hMSH2) gene to a region bordered by markers CA18 and 119 (examples in FIG. 4). The YAC clones listed in Table 1 were then analyzed, and EcoRI and PstI fragments of the expected size identified in YAC 5A11, derived from screening the YAC library with the CA5 marker (FIG. 4).

To confirm the Southern blots, we designed non-degenerate primers on the basis of the sequence of pNP-23. Several sets of primers were tested so that genomic DNA could be used as a template for PCR; an intervening intron prevented the original primers from being used effectively with templates other than cDNA. PCR with these primers was perfectly consistent with the Southern blot results. The expected 101 bp fragment was present in hybrids Z4, Z11, Z29, L1, and L2, and in YAC 5A11, but not in other hybrids or YAC clones (not shown).

The localization of hMSH2 sequences to YAC 5A11 demonstrated the proximity of these sequences to marker CA5. To determine the distance and relative orientation of hMSH2 with respect to CA5, we performed interphase FISH analysis. P1 clones containing CA5, ze3 and hMSH2 sequences (clones 820, 836, and M1015, respectively) were simultaneously hybridized to interphase nuclei following fluorescein and Spectrum Orange labelling (Meltzer et al., 1992). The results demonstrated that MSH2 resides within the HNPCC locus defined by linkage analysis to lie between CA5 and ze3, and less than 0.3 Mb from marker CA5 (FIG. 2E).

cDNA libraries generated from human colon cancer cells or from human fetal brain tissues were then screened with the insert of pNP-23 to obtain additional sequences from this gene. Seventy-five cDNA clones were initially identified and partially sequenced. PCR products representing the ends of the cDNA sequence contig were then used as probes to re-screen the cDNA libraries. This cDNA "walk" was repeated again with the new contig ends. Altogether, 147 cDNA clones were identified. The composite sequence derived from these clones is shown in FIG. 5. An open reading frame (ORF) began 69 nt downstream of the 5' end of the cDNA contig, and continued for 2802 bp. The methionine initiating this ORF was in a sequence context compatible with efficient translation (Kozak, 1986) and was preceded by in-frame termination codons. RNA from placenta and brain were used in a PCR-based procedure (RACE, Frohman et al., 1988) to independently determine the position of the 5' end of hMSH2 transcripts. This analysis demonstrated that the 5' ends of all detectable transcripts were less than 100 bp upstream of the sequence shown in FIG. 5, and were heterogeneous upstream of nt -69. The region of highest homology to the yeast MSH2 gene is shown in FIG. 6. This region encompassed the helix-turn-helix domain perhaps responsible for MutS binding to DNA (Reenan and Kolodner, 1992). The yeast and human MSH2 proteins were 77% identical between codons 615 and 788. There were several other blocks of similar amino acids distributed throughout the length of these two proteins (966 and 934 amino acids in yeast and human, respectively).

Methods cDNA generated from the RNA of colorectal cancer cells with reverse transcriptase was used as template for PCR with the degenerate primers 5'-CTG GAT CCA C(G/A/T/C) G G(G/A/T/C)C C(G/A/T/C)A AT/C)A TG-3' and 5'-CTG GAT CC(G/A) TA(G/A) TG(G/A/T/C) GT (G/A/T/C) (G/A) C(G/A) AA-3'. These two primers were used previously to identify the yeast MSH2 gene and were based on sequences conserved among related mammalian and bacterial genes (Reenan and Kolodner, 1992). The optimal PCR conditions for detecting the human MSH2 gene consisted of 35 cycles at 95° for 30 seconds, 41° for 90 seconds, and 70° for 90 seconds, in the buffer described previously (Sidransky et al., 1991). PCR products were cloned into T-tailed vectors as described (Holton and Graham, 1991) and sequenced with modified T7 polymerase (USB). The insert from one clone (pNP-23) containing human sequences homologous to the yeast MSH2 gene was then used to screen cDNA libraries generated from RNA of SW480 colon cancer cells (Clontech) or of fetal brain (Stratagene). After two further rounds of screening, positive clones were converted into plasmids and sequenced using modified T7 polymerase (Kinzler et al., 1991). In some cases, the inserts were amplified using one hMSH2-specific primer and one vector-specific primer, and then sequenced with SequiTherm Polymerase (Epicentre Technologies). To determine the 5' end of MSH2 transcripts, RACE was performed (Frohman et al., 1989) using brain and placenta cDNA (Clontech).

Example 6

Mutations of hMSH2

The physical mapping of hMSH2 to the HNPCC locus was intriguing but could not prove that this gene was responsible for the disease. To obtain more compelling evidence, we determined whether germ line mutations of hMSH2 were present in the two HNPCC kindreds that originally established linkage to chromosome 2 (Peltomaki et al., 1993a). Intron-exon borders within the most conserved region of hMSH2 (FIG. 6) were determined by sequencing genomic PCR fragments containing adjacent exons. Genomic DNA samples from the lymphocytes of affected members of these two kindreds were then used as templates for PCR to determine the sequence of this domain. The DNA from individual J-42, afflicted with colon and endometrial cancer at ages 42 and 44, respectively, was found to contain one allele with a C to T transition at codon 622 (CCA to CTA), resulting in a substitution of leucine for proline (FIG. 7, top). Twenty additional DNA samples from unrelated individuals all encoded proline at this position. Twenty one members of the J kindred were then analyzed by direct sequencing of PCR products. All eleven affected individuals contained one allele with a C to T transition in codon 622, while all ten unaffected members contained two normal alleles, thus documenting perfect segregation with disease. Importantly, this proline was at a highly conserved position, the identical residue being found in all known MutS related genes from prokaryotes and eukaryotes (FIG. 6 and Reenan and Kolodner, 1992).

No mutations of the conserved region of MSH2 were identified in kindred C, so we next examined other parts of the hMSH2 transcript. RNA was purified from lymphoblastoid cells of patient C-202, a 27 year old male with colon cancer. Reverse transcriptase coupled PCR (RT-PCR) was used to generate four hMSH2-specific products encompassing codons 89 to 934 from this RNA (see Experimental Procedures). An abnormal, smaller RT-PCR product was identified with one of the primer pairs used. Mapping and sequencing studies using various MSH2 primers showed that the abnormal product was the result of a presumptive splicing defect which removed codons 265 to 314 from the hMSH2 transcript. The abnormal transcript was found to segregate with disease in the C kindred, and was not found in twenty unrelated individuals.

We next wished to determine whether hMSH2 was altered in one of the more recently linked families (R. P. and M. N-L., unpublished data), and chose kindred 8 for detailed analysis. DNA and RNA were obtained from lymphoblastoid cells of 8–143, a 42 year old male with colon cancer. The conserved region of hMSH2 was amplified from genomic DNA using PCR and directly sequenced. A T to C substitution was noted in the polypyrimidine tract upstream of the exon beginning at codon 669 (at intron position −6). However, this substitution was also found in two of twenty unrelated, normal individuals, and was therefore a polymorphism unrelated to the disease, with an allele frequency of 0.05. Most of the hMSH2 coding region was then amplified by RT-PCR, as described above, and no abnormal transcripts were detected. Sequencing of the PCR products, however, revealed a C to T transition at codon 406 (CGA to TGA) causing substitution of a termination codon for an arginine residue. RNA was available from the lymphocytes of a second affected member of kindred 8, and the same stop codon was identified. This alteration was not found in twenty other, unrelated individuals.

Finally, we wished to determine whether mutations of this gene occurred in RER+ tumors from patients without evident family histories of cancer. The conserved region of MSH2 was studied in four colorectal tumor cell lines from such patients using genomic DNA as templates for PCR. One tumor (from patient Cx10) was found to contain two hMSH2 alterations. The first was a C to T transition in codon 639 (CAT to TAT), resulting in a substitution of tyrosine for histidine. This change was not found in any of twenty samples from unrelated individuals, but was present in the DNA from normal colon of this patient, and was therefore likely to represent a germ line change (FIG. 7, middle). Like the missense mutation in the J kindred, the Cx10, alteration was at a position perfectly conserved in all MutS homologs (FIG. 6 and Reenan and Kolodner, 1992). The second alteration in the tumor from Cx10, was a substitution of a GT dinucleotide for an A in codon 663 (ATG to TGTG). The resultant one bp insertion was predicted to cause a frameshift, producing a termination codon 36 nt downstream. This mutation was demonstrated in both RNA and DNA purified from the Cx10 tumor, but was not present in the patient's normal colon, so represented a somatic mutation (FIG. 7, bottom). The PCR products from Cx10 were cloned and sequenced, and the insertion mutation at codon 663 and the transition at codon 639 were shown to reside on different alleles.

Methods

To detect mutations, PCR products were generated from cDNA and human genomic DNA templates, then sequenced directly using SequiTherm™. In some cases, the PCR products were cloned into T-tailed vectors for sequencing to confirm the direct sequencing data. The primers used to amplify the conserved region of MSH2 from genomic DNA were 5'-CCA CAA TGG ACA CTT CTG C-3' and 5'-CAC CTG TTC CAT ATG TAC G-3', resulting in a 1.4 kb fragment containing hMSH2 codons 614 to 705, and primers 5'-AAA ATG GGT TGC AAA CAT GC-3' and 5'-GTG ATA GTA CTC ATG GCC C-3', resulting in a 2.0 kb fragment containing MSH2 cDNA codons 683 to 783. Primers for RT-PCR were 5'-AGA TCT TCT TCT GGT TCG TC-3' and 5'-GCC AAC AAT AAT TTC TGG TG-3' for codons 89 to 433, 5'-TGG ATA AGA ACA GAA TAG AGG-3' and 5'-CCA CAA TGG ACA CTT CTG C-3' for codons 350–705, 5'-CAC CTG TTC CAT ATG TAC G-3' and 5'-AAA ATG GGT TGC AAA CAT GC-3' for codons 614 to 783, and 5'-GTG ATA GTA CTC ATG GCC C-3' and 5'-GAC AAT AGC TTA TCA ATA TTA CC-3' for codons 683–949.

Discussion

Three major conclusions can be drawn from the examples described here. First, physical mapping and linkage analysis localized the HNPCC locus on chromosome 2 to an 0.8 Mb segment bordered by markers CA5 and ze3. Second, a new human homolog of the yeast MSH2 gene was identified, and this gene shown to lie in the same 0.8 Mb interval. Third, alterations of the hMSH2 gene occurred in the germ line of patients with RER$^+$ tumors, with or without classical HNPCC, and additional somatic alterations of this gene occurred in tumors (Summarized in Table I). The alterations were at highly conserved regions or significantly altered the expected gene product and thus represent mutations with important functional effects. These results indicate that mutations of hMSH2 are responsible for HNPCC and the RER$^+$ positive phenotype found in tumors.

These data have substantial implications for understanding the neoplastic disease observed in HNPCC. In particular, they suggest that the microsatellite alterations previously observed in tumors from these patients are not epiphenomena, but are intrinsically related to pathogenesis. Additionally, the mutations observed in yeast and bacteria with defective MutS-related genes are not confined to insertions and deletions at simple repeated sequences, though these sequences provide convenient tools for analysis (Modrich, 1991). Similarly, one would expect that many mutations, in addition to microsatellite insertions or deletions, would be found in HNPCC tumors. This could lead to the multiple, sequential mutations in oncogenes and tumor suppressor genes which have been shown to drive colorectal tumorigenesis (Fearon and Vogelstein, 1990). Thus, the molecular pathogenesis of HNPCC tumors is likely to be similar to that occurring in non-HNPCC cases, though accelerated by the increased rate of mutation associated with mismatch repair defects. Accordingly, colon tumors from HNPCC patients have been shown to contain mutations of APC, p53 and RAS at frequencies similar to those found in sporadic colorectal cancers (Aaltonen et al., 1993).

Colorectal tumors from HNPCC patients are distinguished by their relatively normal cytogenetic composition (Kouri et al., 1990), and sporadic, RER$^+$ tumors have been demonstrated to have substantially fewer chromosome losses than those occurring in RER$^-$ cases (Thibodeau et al., 1993; Aaltonen et al., 1993). These data suggest that genetic heterogeneity is critical for colorectal cancer development, but can be generated in two different ways (Thibodeau et al., 1993). Most commonly, it develops through gross alterations resulting in aneuploidy, as suggested nearly eighty years ago (Boveri, 1914). In HNPCC-derived tumors and RER$^+$ sporadic tumors, the diversity is presumably more subtle, consisting of multiple small sequence changes distributed throughout the genome. The latter mechanism of generating diversity may be less dangerous to the host, as HNPCC patients, as well as patients with RER$^+$ sporadic tumors, appear to have a better prognosis than would be expected from histopathologic analysis of their tumors (Ionov et al.,; 1993; Thibodeau et al., 1993; Lothe et al., 1993; Lynch et al., 1993).

References

Aaltonen, L. A., Peltomaki, P., Leach, F. S., Sistonen, P., Pylkkanen, L., Mecklin, J-P., Jarvinen, H., Powell, S. M., Jen, J., Hamilton, S. R., Petersen, G. M., Kinzler, K. W., Vogelstein, B., and de la Chapelle, A. (1993). Clues to the pathogenesis of familial colorectal cancer. Science 260, 812–816.

Baylin, S. B., Makos, M., Wu, J., C-Y, R-W., de Bustros, A., Vertino, P., and Nelkin, B. D. (1991). Abnormal patterns of DNA methylation in human neoplasia: Potential consequences for tumor progression. Cancer Cells 3, 383, 390.

Boveri, T. (1914). Zur Frage der Entstehung maligner tumoren. Gustave Fischer Verlag, Jena, Vol. 1.

Chen, D. J., Park, M. S., Campbell, E., Oshimura, M., Liu, P., Zhao, Y., White, B. F., and Siciliano, M. J. (1992). Assignment of a human DNA double-strand break repair gene (XRCC5) to chromosome 2. Genomics 13, 1088–1094.

Chen, D. J., Marrone, B.., Nguyen, T., Stackhouse, M., Zhao, Y., and Sicilano, J. J., (1994). Regional assignment of a human radiation repair gene (XRCC5) to 2q35 by X-ray hybrid mapping. Genomics, in press.

Egan, S. E., and Weinberg, R. A. (1993). The pathway to signal achievement. Nature 365, 781–783.

Elledge, S. J., Mulligan, J. T., Ramer, S. W., Spottswood, M., and Davis R. W. (1991). Lambda YES: a multifunctional cDNA expression vector for the isolation of genes by complementation of yeast and *Escherichia coli* mutations. Proc. Natl. Acad. Sci. USA 88, 1731–1735.

Fang, W.-h. and P. Modrich (1993). Human strand-specific mismatch repair occurs by a bidirectional mechanism similar to that of the bacterial reaction. J. Biol. Chem. 268, 11838–11844.

Fearon, E. R., and Vogelstein, B. (1990). A genetic model for colorectal tumorigenesis. Cell 61, 759–767.

Frohman, M. A, Dush, M. K., and Martin, G. R. (1988). Rapid production of full-length cDNAs from rare transcripts: Amplification using a single gene-specific oligonucleotide primer. Proc. Natl. Acad. Sci. USA 85, 8998–9002.

Goelz, S. E., Hamilton, S. R., and Vogelstein, B. Purification of DNA from Formaldehyde Fixed and Paraffin Embedded Human Tissue. (1985a). Biochem. Biophys. Res. Commun. 130, 118–126.

Goelz, S. E., Vogelstein, B., Hamilton, S. R., and Feinberg, A. P. Hypomethylation of DNA from Benign and Malignant Human Colon Neoplasms. (1985b). Science 228, 187–190.

Guan, X.-Y., Trent, J. M., and Meltzer, P. S. (1993). Generation of band-specific painting probes from a single microdissected chromosome. Human Molecular Genetics 2, 1117–1121.

Han, H-J., Yanagisawa, A., Kato, Y., Park, J-G., and Nakamura, Y. (1993). Genetic instability in pancreatic cancer and poorly differentiated type of gastric cancer. Cancer Research 53, 5087–5089.

Hanash, S. M., Beretta, L., Barcroft, C. L., Sheldon, S., Glover, T. W., Ungar, D., and Sonenberg, N. (1993). Mapping of the gene for interferon-inducible dsRNA-dependent protein kinase to chromosome region 2p21-22: A site of rearrangements in myeloproliferative disorders. Genes, Chromosomes & Cancer 8, 34–37.

Holmes, J., S. Clark and P. Modrich (1990). Strand-specific mimsatch correction in nuclear extracts of human and *Drosophila melanogaster* cell lines. Proc. Natl. Acad. Sci. U.S.A. 87, 5837–5841.

Holton, T. A., and Graham, M. W. (1991). A simple and efficient method for direct cloning of PCR products using ddT-tailed vectors. Nucleic Acids Research 19, 1156.

Ionov, Y. M., Peinado, A., Malkhosyan, S., Shibata, D., and Perucho M. (1993). Ubiquitous somatic mutations in simple repeated sequences reveal a new mechanism for colonic carcinogenesis. Nature 363, 558–561.

Jass, J. R., Stewart, S. M. (1992). Evolution of hereditary non-polyposis colorectal cancer. Gut 33, 783–786.

Joslyn, G., Carlson, M., Thilveris, A., Albertsen, H., Gelbert, L., Samowitz, W., Groden, J., Stevens, J., Spirio, L., Robertson, M., Sargeant, L., Krapcho, K., Wolff, E., Burt, R., Hughes, J. P., Warrington, J., McPherson, J., Wasmuth, J., Le Paslier, D., Abderrahim, H., Cohen, D., Leppert, M., and White, R. (1991). Identification of deletion mutations and three new genes at the familial polyposis locus. Cell 66, 601–613.

Kao, F-T., and Yu, J-W. (1991). Chromosome microdissection and cloning in human genome and genetic disease analysis. Proc. Natl. Acad. Sci. USA 88, 1844–1848.

Kinzler, K. W., Nilbert, M. C., Su, L.-K., Vogelstein, B., Bryan, T. M., Levy, D. B., Smith, K. J., Preisinger, A. C., Hedge, P., McKechnie, D., Finniear, R., Markham, A., Groffen, J., Boguski, M. S., Altschul, S. F., Horii, A., Ando, H., Miyoshi, Y., Miki, Y., Nishisho, I., Nakamura, Y. Identification of FAP Locus Genes from Chromosome 5q21. (1991). Science 253, 661–665.

Kouri, M., Laasonen, A., Mecklin, J. P., Jarvinen, H., Franssila, K., Pyrhonen, S. (1990). Diploid predominance in hereditary nonpolyposis colorectal carcinoma evaluated by flow cytometry. Cancer 65, 1825–1829.

Kozak, M. (1986). Point mutations define a sequence flanking the AUG initiator codon that modulates translation by Eukaryotic Ribosomes. Cell 44, 283–292.

Kramer, W., Kramer, B., Williamson, M. S., Fogel, S. (1989). Cloning and nucleotide sequence of DNA mismatch repair gene PMS1 from *Saccharomyces cerevisiae*: homology of PMS1 to procaryotic MutL and HexB. Journal of Bacteriology 171, 5339–5346.

Knudson, A. G. (1993). All in the (cancer) family. Nature Genetics 5, 103–104.

Kunkel, T. A. (1993). Slippery DNA and diseases. Nature 365, 207–208.

Lathrop, G. M., Lalouel, J. M., Julier, C., and Ott, J. (1984). Strategies for multilocus linkage analysis in humans. Proc. Natl. Acad. Sci. USA 81, 3443–3446.

Lengyel, P. (1993). Tumor-suppressor genes: News about the interferon connection. Proc. Natl. Acad. Sci. USA 90, 5893–5895.

Levinson, G., and Gutman, G. A. (1987). High frequencies of short frameshifts in poly-CA/TG tandem repeats borne by bacteriophage M13 in *Escherichia coli* K-12. Nucleic Acids Research 15, 5323–5338.

Lindblom, A., Tannergard, P., Werelius, B., and Nordenskjold, M. (1993). Genetic mapping of a second locus predisposing to hereditary non-polyposis colon cancer. Nature Genetics 5, 279–282.

Lothe, R. A., Peltomaki, P., Meling, G-I., Aaltonen, L. A., Nystrom-Lahti, M., Pylkkanen, L., Heimdal, K., Andersen, T. I., Moller, P., Rognum, T. O., Fossa, S. D., Haldorsen, T., Langmark, F., Bragger, A., de la Chapelle, A., and Barresea, A-L. (1993). Genomic instability in colorectal caner: Relationship to clinicopathological variables and family history. Cancer Research, in press.

Lynch, H. T., Omaha, M. W., Shaw, M. D. (1966). Hereditary factors in cancer. Arch Intern Med 117, 206–212.

Lynch, H. T., Smyrk, T. C., Watson, P., Lanspa, S. J., Lynch, J. F., Lynch, P. M., Cavalieri, R. J., and Boland, C. R. (1993). Genetics, natural history, tumor spectrum, and pathology of hereditary nonpolyposis colorectal cancer: An updated review. Gastroenterology 104, 1535–1549.

Meltzer, P. S., Guan, X-Y., Burgess, A., and Trent, J. M. (1992). Rapid generation of region specific probes by chromosome microdissection and their application. Nature Genetics 1, 24–28.

Meurs, E., Chong, K., Galabru, J., Thomas, N. S. B., Kerr, I. M., Williams, B. R. G., and Hovanessian, A. G. (1990). Molecular cloning and characterization of the human double-stranded RNA-activated protein kinase induced by interferon. Cell 62, 379–390.

Modrich, P. (1991). Mechanisms and biological effects of mismatch repair. Ann. Rev. Genet. 25, 229–253.

Peinado, M. A., Malkhosyan, S., Velazquez, A., and Perucho, M. (1992). Isolation and characterization of allelic losses and gains in colorectal tumors by arbitrarily primed polymerase chain reaction. Proc. Natl. Acad. Sci. USA 89, 10065–10069.

Peltomaki, P., Aaltonen, L. A., Sistonen, P., Pylkkanen, L., Mecklin, J-P., Jarvinen, H., Green, J. S., Jass, J. R., Weber, J. L., Leach, F. S., Petersen, G. M., Hamilton, S. R., de la Chapelle, A., and Vogelstein, B. (1993a). Genetic mapping of a locus predisposing to human colorectal cancer. Science 260, 810–812.

Pukkila, P. J., Petseon, J., Herman, G., Modrich, P., and Meselson, M. (1983). Effects of high levels of DNA adenine methylation on methyl-directed mismatch repair in *Escherichia coli*. Genetics 104, 571–582.

Reenan, R. A., Kolodner, R. D. (1992). Isolation and characterization of two *Saccharomyces cerevisiae* genes encoding homologs of the bacterial HexA and MutS mismatch repair proteins. Genetics 132, 963–973.

Risinger, J. I., Berchuck, A., Kohler, M. F., Watson, P., Lynch, H. T., and Boyd, J. (1993). Genetic instability of microsatellites in endometrial carcinoma. Cancer Research 53, 5100–5103.

Sidransky, D., von Eschenbach, A., Tsai, Y. C., Jones, P., Summerhayes, I., Marshall, F., Paul, M., Green, P., Hamilton, S. R., Frost, P., Vogelstein, B. (1991). Identification of p53 Gene Mutations in Bladder Cancers and Urine Samples. Science 252, 706–709.

Spurr, N. K., Cox, S., Naylor, S. (1993). Report and abstracts of the Second International Workshop on human chromosome 2 mapping. Cytogenetics & Cell Genetics 64, 69–92.

Stanbridge, E. J. (1990). Human tumor suppressor genes. Ann. Rev. Genes 24, 615–657.

Strand, M., Prolla, T. A., Liskay, R. M., and Petes, T. D. (1993). Destabilization of tracts of simple repetitive DNA in yeast by mutations affecting DNA mismatch repair. Nature 365, 274–276.

Thibodeau, S. N., Bren, G., and Schaid, D. (1993). Microsatellite instability in cancer of the proximal colon. Science 260, 816–819.

Thomas, D. C., J. D. Roberts and T. A. Kunkel (1991). Heteroduplex repair in extracts of human HeLa cells. J. Biol. Chem. 266, 3744–3751.

Trask, B., Pinkel, D., and van den Engh, G. (1989). The proximity of DNA sequences in interphase cell nuclei is correlated to genomic distance and permits ordering of cosmids spanning 250 kilbase pairs. Genomics 5, 710–717.

Viskochil, D., Buchberg, A. M., Xu, G., Cawthon, R., Stevens, J., Wolff, R. K., Culver, M., Carey, J. C., Copeland, N. G., Jenkins, N. A., White, R., and O'Connell, P. (1990). Deletions and a translocation interrupt a cloned gene at the neurofibromatosis type 1 locus. Cell 62, 187–192.

Vogelstein, B., Fearon, E. R., Hamilton, S. R., Preisinger, A. C., Willard, H. F., Michelson, A. M., Riggs, A. D., and Orkin, S. H. (1987). Clonal Analysis Using Recombinant DNA Probes from the X Chromosome. Cancer Research 47, 4806–4813.

Wallace, M. R., Marchuk, D. A., Andersen, L. B., Letcher, R., Odeh, H. M., Saulino, A. M., Fountain, J. W., Brereton, A., Nicholson, J., Mitchell, A. L., Brownstein, B. H., Collins, F. S. (1990). Type 1 neurofibromatosis gene: Identification of a large transcript disrupted in three NF1 patients. Science 249, 181–186.

Warthin, A. S. (1913). Heredity with reference to carcinoma: As shown by the study of the cases examined in the pathological laboratory of the University of Michigan, 1895–1913. Arch. Int. Med 12, 546–555.

Watson, P., and Lynch, H. T. (1993). Extracolonic cancer in hereditary nonpolyposis colorectal cancer. Cancer 71, 677–685.

Webb, G. C., Jenkins, N. A., Largaespada, D. A., Copeland, N. G., Fernandez, C. S., and Bowtell, D. D. L. (1993). Mammalian homologues of the Drosophila Son of sevenless gene map to murine chromosomes 17 and 12 and to human chromosomes 2 and 14, respectively. Genomics 18, 14–19.

Weber, J. L., May P. E. (1989). Abundant class of human DNA polymorphisms which can be typed using the polymerase chain reaction. American Journal of Human Genetics 44, 338–396.

Weissenbach, J., Gyapay, G., Dib, C., Vignal A., Morissette, J., Millasseau, P., Vaysseix, G., and Lathrop, M. (1992). A second-generation linkage map of the human genome. Nature 359, 794–801.

We claim:
1. A method to aid in determining a predisposition to cancer comprising:
testing a protein-containing body sample of a human selected from the group consisting of a biopsy, blood, prenatal tissue, and embryonic tissue to determine if the sample contains a mutant form of hMSH2 protein, wherein the mutant form has a different primary sequence from that shown in SEQ ID NO:2, wherein determination of a mutant form of hMSH2 protein in the body sample suggests a predisposition to cancer in the human.

2. A method to aid in determining a predisposition to cancer comprising:

testing a first protein-containing body sample of a first human selected from the group consisting of a biopsy, blood, prenatal tissue, and embryonic tissue to determine if the sample contains less hMSH2 protein than a second protein-containing body sample of the selected type of a second human, wherein said second human is homozygous for wild-type hMSH2 coding sequences as shown in SEQ ID NO:1, wherein determination that the first body sample contains less hMSH2 protein suggests a predisposition to cancer in the first human.

3. The method of claim 1 or 2 wherein the sample is isolated from prenatal or embryonic cells.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2947 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens ( x i ) SEQUENCE DESCRIPTION: SEQ ID NO:1:

```
GGCGGGAAAC  AGCTTAGTGG  GTGTGGGGTC  GCGCATTTTC  TTCAACCAGG  AGGTGAGGAG      60

GTTTCGACAT  GGCGGTGCAG  CCGAAGGAGA  CGCTGCAGTT  GGAGAGCGCG  GCCGAGGTCG     120

GCTTCGTGCG  CTTCTTTCAG  GGCATGCCGG  AGAAGCCGAC  CACCACAGTG  CGCCTTTTCG     180

ACCGGGGCGA  CTTCTATACG  GCGCACGGCG  AGGACGCGCT  GCTGGCCGCC  CGGGAGGTGT     240

TCAAGACCCA  GGGGGTGATC  AAGTACATGG  GGCCGGCAGG  AGCAAAGAAT  CTGCAGAGTG     300
```

| | | | | | | |
|---|---|---|---|---|---|---|
| TTGTGCTTAG | TAAAATGAAT | TTTGAATCTT | TTGTAAAAGA | TCTTCTTCTG | GTTCGTCAGT | 360 |
| ATAGAGTTGA | AGTTTATAAG | AATAGAGCTG | GAAATAAGGC | ATCCAAGGAG | AATGATTGGT | 420 |
| ATTTGGCATA | TAAGGCTTCT | CCTGGCAATC | TCTCTCAGTT | TGAAGACATT | CTCTTTGGTA | 480 |
| ACAATGATAT | GTCAGCTTCC | ATTGGTGTTG | TGGGTGTTAA | AATGTCCGCA | GTTGATGGCC | 540 |
| AGAGACAGGT | TGGAGTTGGG | TATGTGGATT | CCATACAGAG | GAAACTAGGA | CTGTGTGAAT | 600 |
| TCCCTGATAA | TGATCAGTTC | TCCAATCTTG | AGGCTCTCCT | CATCCAGATT | GGACCAAAGG | 660 |
| AATGTGTTTT | ACCCGGAGGA | GAGACTGCTG | GAGACATGGG | GAAACTGAGA | CAGATAATTC | 720 |
| AAAGAGGAGG | AATTCTGATC | ACAGAAAGAA | AAAAGCTGA | CTTTTCCACA | AAAGACATTT | 780 |
| ATCAGGACCT | CAACCGGTTG | TTGAAAGGCA | AAAAGGGAGA | GCAGATGAAT | AGTGCTGTAT | 840 |
| TGCCAGAAAT | GGAGAATCAG | GTTGCAGTTT | CATCACTGTC | TGCGGTAATC | AAGTTTTTAG | 900 |
| AACTCTTATC | AGATGATTCC | AACTTTGGAC | AGTTTGAACT | GACTACTTTT | GACTTCAGCC | 960 |
| AGTATATGAA | ATTGGATATT | GCAGCAGTCA | GAGCCCTTAA | CCTTTTTCAG | GGTTCTGTTG | 1020 |
| AAGATACCAC | TGGCTCTCAG | TCTCTGGCTG | CCTTGCTGAA | TAAGTGTAAA | ACCCCTCAAG | 1080 |
| GACAAAGACT | TGTTAACCAG | TGGATTAAGC | AGCCTCTCAT | GGATAAGAAC | AGAATAGAGG | 1140 |
| AGAGATTGAA | TTTAGTGGAA | GCTTTTGTAG | AAGATGCAGA | ATTGAGGCAG | ACTTTACAAG | 1200 |
| AAGATTTACT | TCGTCGATTC | CCAGATCTTA | ACCGACTTGC | CAAGAAGTTT | CAAAGACAAG | 1260 |
| CAGCAAACTT | ACAAGATTGT | TACCGACTCT | ATCAGGGTAT | AAATCAACTA | CCTAATGTTA | 1320 |
| TACAGGCTCT | GGAAAAACAT | GAAGGAAAAC | ACCAGAAATT | ATTGTTGGCA | GTTTTGTGA | 1380 |
| CTCCTCTTAC | TGATCTTCGT | TCTGACTTCT | CCAAGTTTCA | GGAAATGATA | GAAACAACTT | 1440 |
| TAGATATGGA | TCAGGTGGAA | AACCATGAAT | TCCTTGTAAA | ACCTTCATTT | GATCCTAATC | 1500 |
| TCAGTGAATT | AAGAGAAATA | ATGAATGACT | TGGAAAAGAA | GATGCAGTCA | ACATTAATAA | 1560 |
| GTGCAGCCAG | AGATCTTGGC | TTGGACCCTG | GCAAACAGAT | TAAACTGGAT | TCCAGTGCAC | 1620 |
| AGTTTGGATA | TTACTTTCGT | GTAACCTGTA | AGGAAGAAAA | AGTCCTTCGT | AACAATAAAA | 1680 |
| ACTTTAGTAC | TGTAGATATC | CAGAAGAATG | GTGTTAAATT | TACCAACAGC | AAATTGACTT | 1740 |
| CTTTAAATGA | AGAGTATACC | AAAAATAAAA | CAGAATATGA | AGAAGCCCAG | GATGCCATTG | 1800 |
| TTAAAGAAAT | TGTCAATATT | TCTTCAGGCT | ATGTAGAACC | AATGCAGACA | CTCAATGATG | 1860 |
| TGTTAGCTCA | GCTAGATGCT | GTTGTCAGCT | TGCTCACGT | GTCAAATGGA | GCACCTGTTC | 1920 |
| CATATGTACG | ACCAGCCATT | TTGGAGAAAG | GACAAGGAAG | AATTATATTA | AAAGCATCCA | 1980 |
| GGCATGCTTG | TGTTGAAGTT | CAAGATGAAA | TTGCATTTAT | TCCTAATGAC | GTATACTTTG | 2040 |
| AAAAAGATAA | ACAGATGTTC | CACATCATTA | CTGGCCCCAA | TATGGGAGGT | AAATCAACAT | 2100 |
| ATATTCGACA | AACTGGGGTG | ATAGTACTCA | TGGCCCAAAT | TGGGTGTTTT | GTGCCATGTG | 2160 |
| AGTCAGCAGA | AGTGTCCATT | GTGGACTGCA | TCTTAGCCCG | AGTAGGGCT | GGTGACAGTC | 2220 |
| AATTGAAAGG | AGTCTCCACG | TTCATGGCTG | AAATGTTGGA | AACTGCTTCT | ATCCTCAGGT | 2280 |
| CTGCAACCAA | AGATTCATTA | ATAATCATAG | ATGAATTGGG | AAGAGGAACT | TCTACCTACG | 2340 |
| ATGGATTTGG | GTTAGCATGG | GCTATATCAG | AATACATTGC | AACAAAGATT | GGTGCTTTTT | 2400 |
| GCATGTTTGC | AACCCATTTT | CATGAACTTA | CTGCCTTGGC | CAATCAGATA | CCAACTGTTA | 2460 |
| ATAATCTACA | TGTCACAGCA | CTCACCACTG | AAGAGACCTT | AACTATGCTT | TATCAGGTGA | 2520 |
| AGAAGGTGT | CTGTGATCAA | AGTTTTGGGA | TTCATGTTGC | AGAGCTTGCT | AATTTCCCTA | 2580 |
| AGCATGTAAT | AGAGTGTGCT | AAACAGAAAG | CCCTGGAACT | TGAGGAGTTT | CAGTATATTG | 2640 |
| GAGAATCGCA | AGGATATGAT | ATCATGGAAC | CAGCAGCAAA | GAAGTGCTAT | CTGGAAAGAG | 2700 |

| AGCAAGGTGA | AAAAATTATT | CAGGAGTTCC | TGTCCAAGGT | GAAACAAATG | CCCTTTACTG | 2760 |
| AAATGTCAGA | AGAAAACATC | ACAATAAAGT | TAAAACAGCT | AAAAGCTGAA | GTAATAGCAA | 2820 |
| AGAATAATAG | CTTTGTAAAT | GAAATCATTT | CACGAATAAA | AGTTACTACG | TGAAAAATCC | 2880 |
| CAGTAATGGA | ATGAAGGTAA | TATTGATAAG | CTATTGTCTG | TAATAGTTTT | ATATTGTTTT | 2940 |
| ATATTAA | | | | | | 2947 |

( 2 ) INFORMATION FOR SEQ ID NO:2:

( i ) SEQUENCE CHARACTERISTICS:
        ( A ) LENGTH: 934 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
        ( A ) ORGANISM: Homo sapiens ( x i ) SEQUENCE DESCRIPTION: SEQ ID NO:2:

| Met | Ala | Val | Gln | Pro | Lys | Glu | Thr | Leu | Gln | Leu | Glu | Ser | Ala | Ala | Glu |
| 1 | | | | 5 | | | | | 10 | | | | | 15 | |
| Val | Gly | Phe | Val | Arg | Phe | Phe | Gln | Gly | Met | Pro | Glu | Lys | Pro | Thr | Thr |
| | | | 20 | | | | 25 | | | | | 30 | | | |
| Thr | Val | Arg | Leu | Phe | Asp | Arg | Gly | Asp | Phe | Tyr | Thr | Ala | His | Gly | Glu |
| | | 35 | | | | | 40 | | | | | 45 | | | |
| Asp | Ala | Leu | Leu | Ala | Ala | Arg | Glu | Val | Phe | Lys | Thr | Gln | Gly | Val | Ile |
| | 50 | | | | | 55 | | | | | 60 | | | | |
| Lys | Tyr | Met | Gly | Pro | Ala | Gly | Ala | Lys | Asn | Leu | Gln | Ser | Val | Val | Leu |
| 65 | | | | | 70 | | | | | 75 | | | | | 80 |
| Ser | Lys | Met | Asn | Phe | Glu | Ser | Phe | Val | Lys | Asp | Leu | Leu | Leu | Val | Arg |
| | | | | 85 | | | | | 90 | | | | | 95 | |
| Gln | Tyr | Arg | Val | Glu | Val | Tyr | Lys | Asn | Arg | Ala | Gly | Asn | Lys | Ala | Ser |
| | | | 100 | | | | | 105 | | | | | 110 | | |
| Lys | Glu | Asn | Asp | Trp | Tyr | Leu | Ala | Tyr | Lys | Ala | Ser | Pro | Gly | Asn | Leu |
| | | | 115 | | | | | 120 | | | | | 125 | | |
| Ser | Gln | Phe | Glu | Asp | Ile | Leu | Phe | Gly | Asn | Asn | Asp | Met | Ser | Ala | Ser |
| | | 130 | | | | | 135 | | | | | 140 | | | |
| Ile | Gly | Val | Val | Gly | Val | Lys | Met | Ser | Ala | Val | Asp | Gly | Gln | Arg | Gln |
| 145 | | | | | 150 | | | | | 155 | | | | | 160 |
| Val | Gly | Val | Gly | Tyr | Val | Asp | Ser | Ile | Gln | Arg | Lys | Leu | Gly | Leu | Cys |
| | | | | 165 | | | | | 170 | | | | | 175 | |
| Glu | Phe | Pro | Asp | Asn | Asp | Gln | Phe | Ser | Asn | Leu | Glu | Ala | Leu | Leu | Ile |
| | | | 180 | | | | | 185 | | | | | 190 | | |
| Gln | Ile | Gly | Pro | Lys | Glu | Cys | Val | Leu | Pro | Gly | Gly | Glu | Thr | Ala | Gly |
| | | | 195 | | | | 200 | | | | | 205 | | | |
| Asp | Met | Gly | Lys | Leu | Arg | Gln | Ile | Ile | Gln | Arg | Gly | Gly | Ile | Leu | Ile |
| | 210 | | | | | 215 | | | | | 220 | | | | |
| Thr | Glu | Arg | Lys | Lys | Ala | Asp | Phe | Ser | Thr | Lys | Asp | Ile | Tyr | Gln | Asp |
| 225 | | | | | 230 | | | | | 235 | | | | | 240 |
| Leu | Asn | Arg | Leu | Leu | Lys | Gly | Lys | Lys | Gly | Glu | Gln | Met | Asn | Ser | Ala |
| | | | | 245 | | | | | 250 | | | | | 255 | |
| Val | Leu | Pro | Glu | Met | Glu | Asn | Gln | Val | Ala | Val | Ser | Ser | Leu | Ser | Ala |
| | | | 260 | | | | | 265 | | | | | 270 | | |

```
Val  Ile  Lys  Phe  Leu  Glu  Leu  Leu  Ser  Asp  Asp  Ser  Asn  Phe  Gly  Gln
          275                 280                      285

Phe  Glu  Leu  Thr  Thr  Phe  Asp  Phe  Ser  Gln  Tyr  Met  Lys  Leu  Asp  Ile
     290                      295                 300

Ala  Ala  Val  Arg  Ala  Leu  Asn  Leu  Phe  Gln  Gly  Ser  Val  Glu  Asp  Thr
305                      310                 315                           320

Thr  Gly  Ser  Gln  Ser  Leu  Ala  Ala  Leu  Leu  Asn  Lys  Cys  Lys  Thr  Pro
                    325                 330                           335

Gln  Gly  Gln  Arg  Leu  Val  Asn  Gln  Trp  Ile  Lys  Gln  Pro  Leu  Met  Asp
               340                 345                      350

Lys  Asn  Arg  Ile  Glu  Glu  Arg  Leu  Asn  Leu  Val  Glu  Ala  Phe  Val  Glu
          355                 360                      365

Asp  Ala  Glu  Leu  Arg  Gln  Thr  Leu  Gln  Glu  Asp  Leu  Leu  Arg  Arg  Phe
     370                      375                 380

Pro  Asp  Leu  Asn  Arg  Leu  Ala  Lys  Lys  Phe  Gln  Arg  Gln  Ala  Ala  Asn
385                      390                 395                           400

Leu  Gln  Asp  Cys  Tyr  Arg  Leu  Tyr  Gln  Gly  Ile  Asn  Gln  Leu  Pro  Asn
                    405                 410                           415

Val  Ile  Gln  Ala  Leu  Glu  Lys  His  Glu  Gly  Lys  His  Gln  Lys  Leu  Leu
               420                 425                      430

Leu  Ala  Val  Phe  Val  Thr  Pro  Leu  Thr  Asp  Leu  Arg  Ser  Asp  Phe  Ser
          435                 440                      445

Lys  Phe  Gln  Glu  Met  Ile  Glu  Thr  Thr  Leu  Asp  Met  Asp  Gln  Val  Glu
     450                      455                 460

Asn  His  Glu  Phe  Leu  Val  Lys  Pro  Ser  Phe  Asp  Pro  Asn  Leu  Ser  Glu
465                      470                 475                           480

Leu  Arg  Glu  Ile  Met  Asn  Asp  Leu  Glu  Lys  Lys  Met  Gln  Ser  Thr  Leu
                    485                 490                           495

Ile  Ser  Ala  Ala  Arg  Asp  Leu  Gly  Leu  Asp  Pro  Gly  Lys  Gln  Ile  Lys
               500                 505                      510

Leu  Asp  Ser  Ser  Ala  Gln  Phe  Gly  Tyr  Tyr  Phe  Arg  Val  Thr  Cys  Lys
          515                 520                      525

Glu  Glu  Lys  Val  Leu  Arg  Asn  Asn  Lys  Asn  Phe  Ser  Thr  Val  Asp  Ile
     530                      535                 540

Gln  Lys  Asn  Gly  Val  Lys  Phe  Thr  Asn  Ser  Lys  Leu  Thr  Ser  Leu  Asn
545                      550                 555                           560

Glu  Glu  Tyr  Thr  Lys  Asn  Lys  Thr  Glu  Tyr  Glu  Glu  Ala  Gln  Asp  Ala
                    565                 570                           575

Ile  Val  Lys  Glu  Ile  Val  Asn  Ile  Ser  Ser  Gly  Tyr  Val  Glu  Pro  Met
               580                 585                      590

Gln  Thr  Leu  Asn  Asp  Val  Leu  Ala  Gln  Leu  Asp  Ala  Val  Val  Ser  Phe
          595                 600                      605

Ala  His  Val  Ser  Asn  Gly  Ala  Pro  Val  Pro  Tyr  Val  Arg  Pro  Ala  Ile
     610                      615                 620

Leu  Glu  Lys  Gly  Gln  Gly  Arg  Ile  Ile  Leu  Lys  Ala  Ser  Arg  His  Ala
625                      630                 635                           640

Cys  Val  Glu  Val  Gln  Asp  Glu  Ile  Ala  Phe  Ile  Pro  Asn  Asp  Val  Tyr
                    645                 650                           655

Phe  Glu  Lys  Asp  Lys  Gln  Met  Phe  His  Ile  Ile  Thr  Gly  Pro  Asn  Met
               660                 665                      670

Gly  Gly  Lys  Ser  Thr  Tyr  Ile  Arg  Gln  Thr  Gly  Val  Ile  Val  Leu  Met
          675                 680                      685

Ala  Gln  Ile  Gly  Cys  Phe  Val  Pro  Cys  Glu  Ser  Ala  Glu  Val  Ser  Ile
```

|   |   |   |   |   | 690 |   |   |   |   | 695 |   |   |   | 700 |   |
|---|---|---|---|---|---|---|---|---|---|---|---|---|---|---|---|

Val Asp Cys Ile Leu Ala Arg Val Gly Ala Gly Asp Ser Gln Leu Lys
705                710                715                720

Gly Val Ser Thr Phe Met Ala Glu Met Leu Glu Thr Ala Ser Ile Leu
            725                730                735

Arg Ser Ala Thr Lys Asp Ser Leu Ile Ile Ile Asp Glu Leu Gly Arg
            740                745                750

Gly Thr Ser Thr Tyr Asp Gly Phe Gly Leu Ala Trp Ala Ile Ser Glu
            755                760                765

Tyr Ile Ala Thr Lys Ile Gly Ala Phe Cys Met Phe Ala Thr His Phe
        770                775                780

His Glu Leu Thr Ala Leu Ala Asn Gln Ile Pro Thr Val Asn Asn Leu
785                790                795                800

His Val Thr Ala Leu Thr Thr Glu Glu Thr Leu Thr Met Leu Tyr Gln
                805                810                815

Val Lys Lys Gly Val Cys Asp Gln Ser Phe Gly Ile His Val Ala Glu
            820                825                830

Leu Ala Asn Phe Pro Lys His Val Ile Glu Cys Ala Lys Gln Lys Ala
        835                840                845

Leu Glu Leu Glu Glu Phe Gln Tyr Ile Gly Glu Ser Gln Gly Tyr Asp
    850                855                860

Ile Met Glu Pro Ala Ala Lys Lys Cys Tyr Leu Glu Arg Glu Gln Gly
865                870                875                880

Glu Lys Ile Ile Gln Glu Phe Leu Ser Lys Val Lys Gln Met Pro Phe
            885                890                895

Thr Glu Met Ser Glu Glu Asn Ile Thr Ile Lys Leu Lys Gln Leu Lys
            900                905                910

Ala Glu Val Ile Ala Lys Asn Asn Ser Phe Val Asn Glu Ile Ile Ser
        915                920                925

Arg Ile Lys Val Thr Thr
        930

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:3:

CTGGATCCAC NGGNCCNAAY ATG         23

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:4:

CTGGATCCRT ARTGNGTNRC RAA 23

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:5:

CCACAATGGA CACTTCTGC 19

( 2 ) INFORMATION FOR SEQ ID NO:6:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( x i ) SEQUENCE DESCRIPTION: SEQ ID NO:6:

CACCTGTTCC ATATGTACG 19

( 2 ) INFORMATION FOR SEQ ID NO:7:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:7:

AAAATGGGTT GCAAACATGC 20

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:8:

GTGATAGTAC TCATGGCCC 19

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:9:

AGATCTTCTT CTGGTTCGTC     20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:10:

GCCAACAATA ATTTCTGGTG     20

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:11:

TGGATAAGAA CAGAATAGAG G     21

( 2 ) INFORMATION FOR SEQ ID NO:12:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:12:

CCACAATGGA CACTTCTGC     19

( 2 ) INFORMATION FOR SEQ ID NO:13:

( i ) SEQUENCE CHARACTERISTICS:
        ( A ) LENGTH: 19 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:13:

CACCTGTTCC ATATGTACG 19

(2) INFORMATION FOR SEQ ID NO:14:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:14:

AAAATGGGTT GCAAACATGC 20

(2) INFORMATION FOR SEQ ID NO:15:

(i) SEQUENCE CHARACTERISTICS:
(A) LENGTH: 19 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

GTGATAGTAC TCATGGCCC 19

(2) INFORMATION FOR SEQ ID NO:16:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:16:

GACAATAGCT TATCAATATT ACC 23